(12) United States Patent
Huang

(10) Patent No.: US 6,838,447 B2
(45) Date of Patent: Jan. 4, 2005

(54) PARTICULATE COMPOSITIONS FOR CHEMICAL SYNTHESIS

(75) Inventor: Tai-Nang Huang, Lexington, MA (US)

(73) Assignee: Linden Technologies, Inc., Woburn, MA (US)

( * ) Notice: Subject to any disclaimer, the term of this patent is extended or adjusted under 35 U.S.C. 154(b) by 0 days.

(21) Appl. No.: 10/108,212

(22) Filed: Mar. 26, 2002

(65) Prior Publication Data

US 2002/0137719 A1 Sep. 26, 2002

Related U.S. Application Data

(60) Provisional application No. 60/279,004, filed on Mar. 26, 2001, and provisional application No. 60/322,362, filed on Sep. 14, 2001.

(51) Int. Cl.$^7$ .......................... A61K 48/00; C07H 21/04
(52) U.S. Cl. ............................. 514/44; 514/47; 514/48; 514/51; 536/23.2; 435/6
(58) Field of Search ............................. 514/44, 47, 48, 514/51; 536/23.2; 435/6; 425/9

(56) References Cited

U.S. PATENT DOCUMENTS

| | | |
|---|---|---|
| 2,221,776 A | 11/1940 | Carlson |
| 2,297,691 A | 10/1942 | Carlson |
| 2,618,552 A | 11/1952 | Wise |
| 2,874,063 A | 2/1959 | Greig |
| 3,166,432 A | 1/1965 | Gundlach |
| 3,653,893 A | 4/1972 | Jacknow et al. |
| 3,795,617 A | 3/1974 | McCabe |
| 3,957,367 A | 5/1976 | Goel |
| 4,324,851 A | 4/1982 | Lu et al. |
| 4,403,848 A | 9/1983 | Snelling |
| 4,500,707 A | 2/1985 | Caruthers et al. |
| 4,828,979 A | 5/1989 | Klevan et al. |
| 4,956,225 A | 9/1990 | Malhotra |
| 4,973,679 A | 11/1990 | Caruthers et al. |
| 4,997,697 A | 3/1991 | Malhotra |
| 5,047,519 A | 9/1991 | Hobbs, Jr. et al. |
| 5,143,854 A | 9/1992 | Pirrung et al. |
| 5,153,319 A | 10/1992 | Caruthers et al. |
| 5,424,186 A | 6/1995 | Fodor et al. |
| 5,474,796 A | 12/1995 | Brennan |
| 5,529,756 A | 6/1996 | Brennan |
| 5,541,061 A | 7/1996 | Fodor et al. |
| 5,552,471 A | 9/1996 | Woo et al. |
| 5,605,662 A | 2/1997 | Heller et al. |
| 5,667,976 A | 9/1997 | Van Ness et al. |
| 5,672,424 A | 9/1997 | Malhotra et al. |
| 5,677,195 A | 10/1997 | Winkler et al. |
| 5,683,793 A | 11/1997 | Malhotra et al. |
| 5,700,637 A | 12/1997 | Southern |
| 5,714,007 A | 2/1998 | Pletcher et al. |
| 5,723,599 A | 3/1998 | Klem et al. |
| 5,753,302 A | 5/1998 | Sun et al. |
| 5,753,599 A | 5/1998 | Coope et al. |
| 5,780,223 A | 7/1998 | Lupski et al. |
| 5,800,992 A | 9/1998 | Fodor et al. |
| 5,847,105 A | 12/1998 | Baldeschwieler et al. |
| 5,871,010 A | 2/1999 | Datta et al. |
| 5,874,554 A | 2/1999 | Gamble et al. |
| 5,889,165 A | 3/1999 | Fodor et al. |
| 5,897,540 A | 4/1999 | Grundke et al. |
| 5,908,926 A | 6/1999 | Pirrung et al. |
| 5,985,551 A | 11/1999 | Brennan |
| 6,001,311 A | 12/1999 | Brennan |
| 6,004,752 A | 12/1999 | Loewy et al. |
| 6,007,630 A | 12/1999 | Pletcher et al. |
| 6,022,714 A | 2/2000 | Brown et al. |
| 6,028,189 A | 2/2000 | Blanchard |
| 6,045,753 A | 4/2000 | Loewy et al. |
| 6,054,270 A | 4/2000 | Southern |
| 6,074,688 A | 6/2000 | Pletcher et al. |
| 6,117,602 A | 9/2000 | Liu et al. |
| 6,177,558 B1 | 1/2001 | Brennan et al. |
| 6,181,902 B1 | 1/2001 | Kopp |
| 6,210,894 B1 | 4/2001 | Brennan |
| 6,239,273 B1 | 5/2001 | Pease et al. |
| 6,337,393 B1 | 1/2002 | Brennan et al. |
| 6,511,803 B1 | 1/2003 | Church et al. |
| 2001/0044530 A1 | 11/2001 | Huang et al. |
| 2002/0136772 A1 | 9/2002 | Huang |
| 2002/0136978 A1 | 9/2002 | Huang |
| 2002/0137085 A1 | 9/2002 | Herrick |
| 2002/0168669 A1 | 11/2002 | Huang |

FOREIGN PATENT DOCUMENTS

| | | |
|---|---|---|
| WO | WO89/10977 | 11/1989 |
| WO | WO95/25116 | 9/1995 |
| WO | WO98/41531 | 9/1998 |
| WO | WO99/25724 | 5/1999 |
| WO | WO99/28290 | 6/1999 |
| WO | WO99/41007 | 8/1999 |

OTHER PUBLICATIONS

U.S. patent application Ser. No. 10/108,167, Huang, filed Mar. 26, 2002.
U.S. patent application Ser. No. 60/151,158, Herrick, filed Aug. 27, 1999.
Amarnath and Broom, "Chemical Synthesis of Oligonucleotides", *Chemical Reviews*, 77(2):183–217 (1977).
Amit et al., "Photosensitive Protecting Groups of Amino Sugars and Their Use in Glycoside Synthesis. 2–Nitrobenzyloxycarbonylamino and 6–Nitroveratryloxycarbonylamino Derivatives", *J. Org. Chem.*, 39(2):192–196 (1974).
Atkinson et al., in "Oligonucleotide synthesis: a practical approach", MJ Gait, Ed., IRL Press, Washington, DC (1984).
Bannwarth and Iaiza, "Laboratory Methods: A System for the Simultaneous Chemical Synthesis of Different DNA Fragments on Solid Support", *DNA*, 5(5):413–419 (1986).

(List continued on next page.)

*Primary Examiner*—James O. Wilson
*Assistant Examiner*—Ganapathy Krishnan
(74) *Attorney, Agent, or Firm*—Fish & Richardson P.C.

(57) ABSTRACT

Disclosed are compositions that include triboelectrically chargeable nucleotide particles of less than 50 μm diameter and carrier particles. In one example, a substrate is selectively patterned with the compositions, e.g., by transfer from a selectively charged surface. The compositions can be used to synthesize nucleic acid arrays.

15 Claims, 19 Drawing Sheets

OTHER PUBLICATIONS

Basarsky et al., "Overview of a Microarray Scanner: Design Essentials for an Integrated Acquisition and Analysis Platform", in *Microarray Biochip Technology*, Chapter 13, M. Schena, Ed.,Eaton Publishing, Natick, MA (2000).

Beaucage et al., "Advances in the Synthesis of Oligonucleotides by the Phosphoramidite Approach", *Tetrahedron*, 48(12):2223–2311 (1992).

Brown and Botstein, "Exploring the new world of the genome with DNA microarrays", *Nature Genetics Supplement*, 21:33–37 (1999).

Bunin et al., "The combinatorial synthesis and chemical and biological evaluation of a 1,4–benzodiazepine library", *Proc Natl Acad Sci USA*, 91:4708–4712 (1994).

Clause and Mayer, "Liquid Development", in *Xerography and Related Processes*, Chapter 12, ed. Dessauer and Clark (Focal, New York 1965).

DeWitt et al., "Diversomers: An approach to nonpeptide, nonoligomeric chemical diversity", *Proc Nat Acad Sci USA*, 90:6909–6913 (1993).

Fodor et al., "Light–Directed, Spatially Addressable Parallel Chemical Synthesis", *Science*, 251:767–773 (1991).

Fodor et al., "Multiplexed biochemical assays with biological chips", *Nature*, 364:555–556 (1993).

Gerhold et al., "DNA chips: promising toys have become powerful tools", *TIBS*, 24:168–173 (1999).

Hays, in "Xerography", *Encyclopedia of Applied Physics*, American Institute of Physics, 23 (Introduction only) (1998).

Henniker, "Triboelectricity in Polymers", *Nature*, 196:474 (1962).

International Human Genome Sequencing Consortium, "Initial Sequencing and Analysis of the Human Genome", *Nature*, 409:860–921 (2001).

Kruglyak, "Prospects for whole–genome linkage disequilibrium mapping of common disease genes", *Nature Genetics*, 22:139–144 (1999).

Kumar and Poonian, "Improvements in Oligodeoxyribonucleotide Synthesis: Methyl N,N–Dialkylphosphoramidite Dimer Units for Solid Support Phosphite Methodology", *J. Org. Chem.*, 49:4905–4912 (1984).

LeProust et al., "Digital Light–Directed Synthesis. A Microarray Platform That Permits Rapid Reaction Optimization on a Combinatorial Basis", *J. Comb. Chem.*, 2:349–354 (2000).

Lockhart and Winzeler, "Genomics, gene expression and DNA arrays", *Nature*, 405:827–836 (2000).

McBride and Caruthers, "An Investigation of Several Deoxynucleoside Phosphoramidites Useful for Synthesizing Deoxyoligonucleotides", *Tetrahedron Letters*, 24(3):245–248 (1983).

McGall et al., "Light–directed synthesis of high–density oligonucleotide arrays using semiconductor photoresists", *Proc. Natl. Acad. Sci. USA*, 93:13555–13560 (1996).

Merrifield, "Automated Synthesis of Peptides", *Science*, 150:178–185 (1965).

Okamoto et al., "Microarray fabrication with covalent attachment of DNA using Bubble Jet technology", *Nature Biotechnology*, 18:438–441 (2000).

Pai and Springett, "Physics of electrophotography", *Rev. Mod. Phys.*, 65:163–211 (1993).

Ramsay, "DNA Chips: State–of–the art", *Nature Biotechnology*, 16:40–44 (1998).

Shchepinov et al., "Steric factors influencing hybridisation of nucleic acids to oliogonucleotide arrays", *Nucleic Acids Research*, 25:1155–1161 (1997).

Shoemaker et al., "Experimental annotation of the human genome using microarray technology", *Nature*, 409:922–927 (2001).

Singh–Gasson et al., "Maskless fabrication of light–directed oligonucleotide microarrays using a digital micromirror array", *Nature Biotechnology*, 17, 974–978 (1999).

Sonveaux, "The Organic Chemistry Underlying DNA Synthesis", *Bioorganic Chemistry*, 14:274–325 (1986).

Venter et al., "The Sequence of the Human Genome", *Science*, 291:1304–1351 (2001).

Watson et al., "Technology for microarray analysis of gene expression", *Current Opinion in Biotechnology*, 9:609–614 (1998).

Weaver, "High–throughput SNP discovery and typing for genome–wide genetic analysis", *Trends in Genetics*, 36–42 (Dec. 2000).

Sarnoff Corp Web Page, Printed Mar. 12, 2002.

Epping PES Laboratorium, "The q/m–meter", Printed May 18, 2002.

Epping PES Laboratorium, "The Charge Spectrometer q/d meter", Printed May 18, 2002.

Kyocera FS–8000C.

PARTICULATE COMPOSITIONS FOR CHEMICAL SYNTHESIS

CROSS REFERENCE TO RELATED APPLICATIONS

This application claims benefit or priority to U.S. Provisional Patent Application Ser. No. 60/279,004, filed Mar. 26, 2001, and application Ser. No. 60/322,362, filed Sep. 14, 2001, the contents of both of which are incorporated herein by reference in their entirety.

BACKGROUND OF THE INVENTION

The invention relates to the synthesis of arrays of chemical compounds. A variety of chemical compounds can be synthesized on a solid support. Combinatorial libraries of chemical compounds can be synthesized on the solid phase (see, e.g., DeWitt et al. (1993) *Proc Nat Acad USA* 90:6909; and Bunin et al. (1994) 91:4708). For example, Merrifield developed a method for synthesizing peptides on a support (Merrifield (1965) *Science* 150:178–185). This method was extended to oligonucleotides by Letsinger and others (see, e.g., Beaucage and Iyer (1992) *Tetrahedron* 12:2223 for a review). Arrays of chemical compounds can be produced by synthesizing the different compounds on a common solid support, e.g., a planar surface of the support. Such arrays provide a convenient format for analyzing multiple interactions in parallel, and, accordingly, is adaptable for high throughput screening, e.g., for drug discovery, gene discovery, genotyping, and diagnosis.

Arrays can be produced by the in situ synthesis of compounds on the solid support to form the covalent immobilization of compounds are in-situ synthesis of biopolymers from properly protected monomers.

Photolithographic methods (see, e.g., Fodor et al. (1991) *Science* 251:767–773; Fodor et al. (1993) *Nature* 364:555–556; U.S. Pat. No. 5,143,854) have been used to construct oligonucleotide arrays with spatial addressability. This approach, at least in some implementations, uses customized photomasks to control the addition of a particular nucleotide monomer at each successive addition reaction. In another approach, micromirrors (see, e.g., Gao et al. (2000) *J. Comb. Chem.* 2: 349–354; M. R. Sussman et al. (1999) *Nature Biotechnology* 17:974–978; and WO 99/41007) are employed to provide an addressable array of light without the use of a photomask. The light can locally produce acid which subsequently removes the acid labile protecting groups, 4,4'-dimethoxy-trityl (DMT), on nucleotide monomers.

A third approach uses a pulse jet, such as found in an inkjet printer, to distribute sub-nanoliter volume of nucleotide monomer solution and the activation agent such as tetrazole (see, e.g., WO 95/25116, U.S. Pat. Nos. 6,028,189; 5,874,554; 5,474,796; 6,177,558 and WO 98/41531). The piezoelectric pumps deliver, e.g., 5'-protected, 3'-phosphoramidite activated nucleotides dissolved in organic solvent to individual spots on an array. The solution of activated nucleotide is mixed with a solution of a coupling agent to covalently attach the activated nucleotide to a functional group on the glass surface. The 5'-protecting groups are subsequently removed with a deprotecting reagent. The entire process is repeated until the desired oligonucleotides are formed.

In one implementation, five nozzle heads are used for DNA synthesis using the pulse jet method. Four nozzle heads are provided for the four nucleotide monomers A, T, G, C, and a fifth nozzle head is used to deliver a solution of an activating agent for coupling reactions after each nucleotide monomer is printed on the substrate. The accuracy of delivering the activating agent to a location where one of the nucleotide monomers is previously spotted can impact the coupling reaction (see, e.g., U.S. Pat. Nos. 5,985,551 and 5,474,796). The entire apparatus is kept in a moisture-free environment at every step in the process.

SUMMARY

The present invention provides methods of dispensing the nucleic acid subunits as a dry composition (e.g., a particulate composition) for the in-situ synthesis of nucleic acid polymers. Because the dry nucleotide are chemically stable, deposition of the four nucleotide monomers in dry form can be accomplished simultaneously on the same substrate in an open environment, thus, facilitating the synthesis of the biopolymer on a substrate surface. A subunit for polymer synthesis is a compound that can be used to construct a polymer such that at least a portion of the subunit becomes incorporated in the polymer. A typical subunit is a monomer subunit, e.g., a nucleotide for nucleic acid synthesis. Larger subunits that can be used are dinucleotides and oligonucleotiders (e.g., heptamers, and so forth).

In one aspect, the invention features a composition, e.g., a toner composition, that includes chargeable particles of diameter less than about 100, 50, 20, 18, 15, 12, 10, 9, 8, 7, or 6 $\mu$m. The particles include a compound that has a reactive group and a protecting group. The particles can be prepared with additives to improve the physical properties such as triboelectrification. The composition can further include chargeable beads of at least 30, 40, 50, 60, or up to 200 $\mu$m in diameter. The chargeable beads can be larger in diameter than the chargeable particles.

In some embodiment, the compound is a nucleotide or an amino acid. A nucleotide compound can have the protecting group attached at the C-3' or the C-5'. The nucleotide compound can have a reactive group that is phosphoramidite. An amino acid compound can have the protecting group attached to its amino or carboxyl group. The protecting group can be photosensitive, acid-sensitive, or base-sensitive. In some instances, the compound may be a preformed polymer, e.g., a protected dinucleotide or other oligonucleotide that includes a protecting group.

In one aspect, the invention features a composition that includes: particles of less than 100, 50, 30, 20, 10, 7, or 5 $\mu$m diameter, the particles are composed at least partially of a nucleotide that includes a 5' and 3' functional groups (e.g., a protecting group and a phosphoramidite). The particles can be at least 0.02, 0.05, 0.1, or 0.2 $\mu$m in diameter. Typically, one of the functional groups is a protecting group and the other is a reactive group. All nucleotide particles of the composition may be of less than 50 $\mu$m diameter. For example, the composition can be devoid of nuclceotide particles of greater than 10, 20, 30 or 50 $\mu$m diameter. The composition can be a dry composition or a liquid composition.

In one embodiment, the nucleotide particles are between 0.1% and 100%, e.g., 0.1% and 50%, or 1% and 95% of the composition by weight. Viewed, as a percentage weight of the total nucleotide weight in the composition, the nucleotide particles of the given diameter can be at least 20, 40, 50, 60, or 80% of the composition.

The nucleotide can be, e.g., adenine, guanine, cytosine, or thymidine.

In another aspect, the invention features a composition that includes: chargeable particles (e.g., triboelectrically chargeable particles) of less than 50 µm diameter, and carrier particles. The chargeable particles are at least partially composed (e.g., at least 5, 10, 20, 50, 80%) of nucleotide. The composition can be a dry composition.

The nucleotide particles can be positively and/or negatively chargeable to 5 to 50 µC/g or 10 to 30 µC/g, or about 1 to 10 µC/g. The carrier particles can include a metal oxide, e.g., one or more of ferrite, zinc oxide, and nickel oxide. Agitation of the composition can charge the nucleotide particles. The composition itself can be charged or uncharged at a given instance.

The composition can include a surface charge control agent such as polystyrene, polyformaldehyde, polymethylmethacrylate, polyamide, fumed silica, cabosil, amorphous silica, a fluorinated polymer (e.g., Kynar), polyethylene glycol succinate, polyethylene glycol adipate, polydiallyl phthalate, polyurethane elastomer, styreneacrylonitrile copolymer, styrene-butadiene copolymer, polyisobutylene, borosilicate glass, polyethylene glycol terephthalate, epoxide resin, polychlorobutadiene, butadiene-acrylonitrile copolymer, polyacrylonitrile, polyethylene, chlorinated polyether, zinc steric polytrifluorochloroethylene and polytetrafluoroethylene.

In another aspect, the invention features a composition that includes: particles of less than 50, 30, or 10 µm diameter, the particles being at least partially composed of a nucleotide, means for controlling surface charge on the particles; and means for triboelectrically charging the particles.

In still another aspect, the invention includes a composition that includes: a dielectric liquid component and particles. The particles are insoluble in the liquid and are composed of a protected chemical compound, e.g., a nucleotide subunit. The particles of the composition are less than 50, 30, 20, 10, or 7 µm in diameter. The particles can be, for example, between 1 and 40% of the composition, weight to volume. In one embodiment, the dielectric liquid has resistivity of between $10^8$ Ωcm and $10^{12}$ Ωcm. The dielectric liquid can be at least partially composed (e.g., at least 80%, 95%, 100%) of a chemically inert organic solvent, e.g., a high molecular weight aliphatic hydrocarbon solvent such as an isoparaffin. The composition can further include a means for stabilizing charge.

In another aspect, the invention features a method that includes: providing a solid composition composed of a nucleotide monomer subunit that is activated at one terminus and protected at another terminus; processing the solid composition to produce nucleotide particles that are less than 50 µm in average diameter; and combining the nucleotide particles with a carrier agent (e.g., carrier beads such as ferrite carrier beads) to produce a developer composition. In one embodiment, the nucleotide particles are at least 5, 10, 30, 50% of the solid composition by weight.

The processing can include jet milling. The processing can further include isolating particles that are less than 10 µm in diameter. Hence, in some embodiments, the processing produces nucleotide particles that are less than 20, 10, 7, or 5 µm in diameter.

The method can further include combining the nucleotide particles with a surface charge control agent, e.g., an agent described herein, including one or more of: cabosil, fumed silica, a fluorinated polymer, and polystyrene.

In another aspect, the invention features a method that includes: providing a particulate composition (e.g., a toner composition) that includes particles of a chemical compound; triboelectrically charging the particles (e.g., by agitation); contacting the charged particles to a selectively charged surface; and transferring the nucleotide particles from the surface to a substrate. The particulate composition includes: (a) chargeable particles of less than 50 microns diameter, the particles include a chemical compound, e.g., a compound that has an activated group and/or a protecting group, and (b) chargeable carrier beads. The chemical compound can be, e.g., a nucleotide, an oligonucleotide, or an amino acid. In one example, the particles are composed of a nucleotide that has a phosphoramidite group and a protecting group The selectively charged surface can include discrete areas that are electrostatically repel the charged nucleotide particles and other areas to which the charged nucleotide particles attach. The selectively charged surface can be cylindrical, e.g., a drum, or can be non-cylindrical (e.g., a belt). The selectively chargeable surface can be a surface whose charge is altered by illumination, e.g., a photoreceptor.

In one embodiment, the agitating charges the nucleotide particles to between 5 µC/g to 50 µC/g. The toner composition can further include a surface charge control agent.

In another aspect, the invention features a method of coupling a compound to a substrate that has an immobilized reactive group. The method includes forming a dry thin film of a compound having a reactive group and a protecting group on the substrate; and contacting an organic solvent having an activator compound dissolved therein to the substrate to thereby couple the compound to the substrate by coupling the immobilized reactive group to the compound reactive group. An activator compound is a compound that is able to activate a phosphorous activating group such as a phosphoramidite to be come a highly reactive phosphitilating agent so that a nucleotide that includes the phosphorous activating group covalently couples to a receiving group. The activator compound can be a weak acid. Preferably, the activator compound results in near quantitative yield. For example, the activator compound can be tetrazole, 5-(p-nitrophenyl)-1H-tetrazole, 5-ethylthio-1H-tetrazole, 4,5-dichloroimidazole, benzimidazolium triflate, and 4,5 dicyano-imidazole.

In still another aspect, the invention features a method of depositing a chemical compound. The method includes: (1) combining a toner composition that includes chargeable particles of a compound that has a reactive group and a protecting group (e.g., as described herein) with charged carrier beads to generate developer particles; (2) depositing the compound from the developer particles in a loading zone onto a surface region of a photoreceptor, the surface region being selectively activated by illumination; (3) positioning the photoreceptor to displace the surface region from the loading zone into proximity to or contact with a substrate (e.g., via a charge device); and (4) transferring the compound to the substrate.

The compound can be a nucleotide, an oligonucleotide, an amino acid, or another small organic molecule. The method can include repeating steps (1) to (4) for a second compound, e.g., the compound can be different from the first compound.

The method can further include (5) contacting a solvent containing an activator compound to the target substrate, such that the liquid activator agent dissolves the transferred dry compound, catalyzes the coupling of the reactive group of the protected chemical compound to an immobilized group on the target substrate. For example, the activator compound can be tetrazole, 5-(p-nitrophenyl)-1H-tetrazole, 5-ethylthio-1H-tetrazole, 4,5-dichloroimidazole, benzimidazolium triflate, and 4,5 dicyano-imidazole. The solvent can be an aprotic organic solvent, e.g., acetonitrile, dinitriles and other solvent mentioned herein. The organic solvent can be a high-boiling point solvent.

In a method of synthesizing nucleic acids, the method can include repeating steps (1) to (4) for each of four nucleotides. The method can further include optionally (6) contacting the target substrate with a capping reagent, e.g., acetic anhydride in pyridine; optionally (7) oxidation; and (8) exposing the target substrate to a condition that releases the protecting group from the immobilized compound. The method can then include the addition of the next nucleotide to each of the nucleic acids on the target substrate by repeating the method until the array of nucleic acids is complete.

In another aspect, the invention features a method of constructing a nucleic acid array. The method includes: determining a plurality of layer maps from a set of nucleic acid sequences, each layer map corresponding to a particular register and nucleic acid subunit and indicating discrete addresses at which the corresponding nucleic acid subunit is to be coupled; for each register, directing a plurality of applicator units that each are supplied with a different nucleic acid subunit to each transfer the respective nucleic acid subunit to a substrate at the discrete addresses indicated by the layer map for the respective nucleic acid subunit; and coupling the transferred nucleic acid subunits to a reactive terminus to form an array of nucleic acids.

In one embodiment, the reactive terminus is on the surface of the substrate, e.g., the substrate is the target substrate. In another embodiment, the reactive terminus is on the surface of a second substrate, and the nucleic acid subunits are transferred from the first substrate (e.g., an interim substrate) to the second substrate (e.g., the target substrate).

The nucleic acid subunits can be supplied as particles of less than 50 $\mu$m diameter, e.g., a composition described herein. The subunit can be a monomeric subunit.

In one embodiment, each applicator unit includes a photoreceptor, an illumination unit that selectively alters the charge at discrete positions on the photoreceptor, and an agitator that agitates a toner composition comprised of the nucleic acid subunit particles and carrier beads.

In another aspect, the invention features a method that includes: 1) repeating for each of four nucleotide bases, adenine, guanine, cytosine, and thymidine,
  a) triboelectrically charging particles of the respective nucleotide base, the base including a protecting group;
  b) selectively irradiating a photoreceptor to generate a patterned region with defined electrostatic charge;
  c) contacting the charged nucleotide particles to the photoreceptor to attach the particles to the photoreceptor in the patterned region; and
  d) transferring the nucleotide particles from the photoreceptor to a surface; 2) coupling the transferred particles to terminal groups on a solid support; and 3) repeating 1) and 2) to produce a plurality of different nucleic acid sequences on the solid support. The method can be used to provide a nucleic acid array.

In one embodiment, the surface is the surface of an interim substrate and the method further includes transferring the particles from the surface of the interim substrate to the solid support. For example, a different interim substrate can be used for each repetition of 1) and 2)).

In one embodiment, the coupling comprises contacting the particles to an activator compound, e.g., an activator compound described herein.

The cycles of a) to d) can include conveying the substrate (e.g., a flexible substrate) between each of four applicator units, each applicator unit comprising a photoreceptor and a source of the respective nucleotide particles. The substrate can include paper, Mylar, cellulose, polyvinylchloride, and/or polycarbonate.

In another aspect, the invention features an apparatus for depositing chemical compounds on a substrate. The apparatus includes a substrate path, adapted to move a substrate; applicator units; an image roll that includes a photoreceptor surface, a transfer unit, and a chemical fuser. The transfer unit can include a electrical field generator, e.g., a scanning electrical field generator. The transfer unit can include support for positioning an interim substrate in apposition to a target substrate.

The substrate path can be adapted to move the substrate e.g., from the image roll to the transfer unit. Each applicator unit can include a charge pattern generator and a dispenser that deposits charged particles, for example, particles of a chemical compound having a protecting group and a reactive group. The charge pattern generator can include a charger which deposits electrostatic charge on the photoreceptor surface and a light source which selectively illuminates the photoreceptor surface to generate a pattern of electrostatic charge (e.g., a latent image). The light source can be interfaced to a controller, e.g., a computer system programmed with a method described herein. The source can be, for example, a laser or a light-emitting diode array.

The image roll is configured to rotate regions, of the photoreceptor surface between the applicator units and the substrate. For example, the image roll can be a drum or a belt that moves regions of the photoreceptor surface between applicator units and the substrate. The photoreceptor surface is selectively chargeable by light discharged from the charge pattern generator for adherence to the charged particles deposited by the dispenser.

The fuser can be configured to dispense an organic solution or an aerosol thereof onto the target substrate. The organic solution contains an activator compound.

The apparatus can include, for example, 2, 3, 4, 5, 6, 9, 10, 18, 19, 20, 21, 22 or more applicator units. An apparatus adapted to synthesize nucleic acids on a substrate can, for example, have at least four applicator units. An apparatus adapted to synthesize peptides on a substrate can, for example, have about twenty applicator units (e.g., at least ten, fifteen, or nineteen). Further, the apparatus can be adapted to have two or more image rolls, and the applicator units can be distributed among the image rolls. For example, an apparatus adapted to synthesize nucleic acid on a substrate can have two image rolls, each having two applicator units.

In another aspect, the invention features an apparatus for depositing chemical compounds on a substrate. The apparatus includes a substrate path, adapted to move a substrate; photoreceptors, applicator units; registration unit and a chemical fuser. Each photoreceptor is adapted to move a region of its surface from a loading zone of an applicator unit to a position along the substrate path such that the surface can contact a substrate on the path. For example, the photoreceptor can be a cylinder or drum that rotates regions of its surface between the loading zone and the substrate path. In another example, the photoreceptor is a belt.

Each applicator unit can include a charge pattern generator and a dispenser that deposits charged particles, for example, particles of a chemical compound having a protecting group and a reactive group. The charge pattern generator can include a charger which deposits electrostatic charge on the photoreceptor surface and a light emitter which selectively illuminates the photoreceptor surface to generate a pattern of electrostatic charge. The light emitter can be interfaced to a controller, e.g., a computer system programmed with a method described herein.

The dispenser is configured to combine, e.g., with brush, blades, or motors, a toner composition with the carrier beads, and to deposit developer particles that include the carrier beads and a toner composition onto a photoreceptor.

The fuser is adapted to dispense an organic solvent (e.g., containing an activator compound) onto the substrate, as described above and herein.

For example, when adapted for nucleic acid synthesis, the apparatus can include four photoreceptor, each having an applicator unit. The substrate path can position the substrate at each of the four photoreceptors, to receive sequentially all four possible subunit nucleotides. The path can then position the target substrate at the chemical fuser and other optionally post-processing stations, and return the substrate back to the photoreceptors to repeat the process.

In the case of oligonucleotide arrays, only four applicator units, one for each base, are required to produce arrays with flexible sequence composition and spatial arrangement. Unlike the deposition of preformed oligonucleotides, the same four applicators are used in a cyclic manner (e.g., without cleansing and exchange of reagents) to produce any sequence formed from the four canonical bases. As seen, each applicator is dedicated to the deposition of a particular nucleotide (e.g., a nucleotide selected from the deoxyribonucleotides: adenine, guanine, cytosine and thymidine, or in some cases ribonucleotides, in which case uracil may be used).

Although the simple four applicator design is completely versatile for most purposes, additional applicators can be used to add dinucleotides and larger oligomers that are protected and that can be coupled to growing chains, and/or unnatural nucleotides that are protected. Kumar and Pumian (1984) *J. Org. Chem.* 12:3387, e.g., describe coupling with phosphoramidite activated dinucleotides. For example, if an array of primers is being constructed such that the primers all include a universal sequence, the universal sequence can be presynthesized in bulk on a bead using a conventional automated oligonucleotide synthesizer. The oligonucleotide is protected and/or phosphoramidite activated and added to a "fifth" applicator unit. With respect to applications that require an unnatural nucleotide, examples of such unnatural nucleotides include inosine, abasic nucleotides, and nucleotides that include nitro or cyano substituted indoles, (e.g., 3-nitropyrrole nucleotide), e.g., as described in U.S. Pat. No. 5,780,223.

In another aspect, the invention features a method that includes: depositing a nucleotide compound as a particulate composition, the nucleotide compound having a first functional group on a solid support that includes a second functional group attached thereto, and contacting the solid support with an aerosol of a liquid composition that includes, dissolved therein, an activator compound that triggers the coupling of the first functional group to the second functional group. Exemplary activator compounds include: tetrazole, and derivatives thereof, e.g., 5-(p-nitrophenyl)-1H-tetrazole, 5-ethylthio-1H-tetrazole, 4,5-dichloroimidazole, benzimidazolium triflate, or 4,5 dicyanoimidazole. The concentration of the activator compound in the organic solvent can be between 0.1 M and 1.0 M.

In one embodiment, the particulate composition is dry at the instance of the depositing; in another, the particulate composition is suspended in a dielectric liquid (e.g., a chemically inert liquid such as an isoparaffin) at the instance of the depositing.

The liquid composition that is aerosolized can include a high boiling point organic solvent, e.g., propylene carbonate, a dinitrile, or diethyl carbonate. In one embodiment, the liquid composition is a mixture that includes high boiling point organic solvent and a low boiling point organic solvent, e.g., an aprotic solvent, such as methylene chloride or acetonitrile. In one embodiment, the mixture is between 20:80 and 80:20, or 40:60 to 60:40. One exemplary mixture includes propylene carbonate and acetonitrile.

In one embodiment, the nucleotide compound further comprises a protecting group, attached to C-3' or C-5' of the nucleotide residue. The compound can include a phosphoramidite at the other terminus. In another example, the compound includes a hydroxyl group at the other terminus. The protecting group can be photo, acid, or base sensitive.

In one embodiment, the method further includes reacting uncoupled second functional groups with a capping reagent, e.g., an acylating reagent, e.g., acetic anhydride.

In another aspect, the invention features a method that includes: depositing, on a solid support, different nucleic acid subunits at different addresses, and contacting a section of the solid support with an aerosol of an organic solvent that includes an activator reagent dissolved therein. At least a plurality of addresses within the section can be concurrently contacted by the aerosol. The activator reagent triggers the coupling of the nucleic acid subunit to a group attached to the support. The long axis of the contacted section can be at least 0.02 meters, e.g., a section of at least 0.04 by 0.04 meters, 0.04 by 0.1 meters, or 0.1 by 0.15 meters. The nucleic acid subunit can include a protecting group.

In one embodiment, the nucleic acid subunits are dissolved in a low boiling point solvent. The method can include evaporating the low boiling point solvent prior to contacting the solid support with an aerosol of organic solvent, e.g., to form a dry thin film is formed by the evaporating. In another embodiment, the nucleic acid subunits are deposited as a particulate composition.

In another aspect, the invention features a method that includes: depositing a nucleotide compound dissolved in a low boiling point solvent, the nucleotide compound having a first functional group, on a solid support that includes a second functional group attached thereto, and contacting the solid support with an aerosol of a liquid composition that includes, dissolved therein, an activator compound that triggers the coupling of the first functional group to the second functional group, wherein the liquid composition is a mixture of a low boiling point solvent and a high boiling point solvent.

In still another aspect, the invention features a method that includes: forming a dry deposition (e.g., a thin film or a particulate deposition) of a compound (e.g., a nucleotide residue) having a first reactive group (e.g., a hydroxyl or phosphoramidite) on a substrate, wherein the substrate has an immobilized second reactive group, and contacting an organic solvent to the substrate, the solvent having an activator compound dissolved therein, thereby immobilizing the compound to the substrate by coupling the first and second reactive groups. The nucleotide residue can include a C-3' or C-5' protecting group.

In one embodiment, the method further includes reacting uncoupled second reactive groups with a capping reagent.

The forming can include depositing the compound dissolved in a low boiling point solvent onto the substrate, and evaporating the low boiling point solvent.

In one embodiment, the first reactive group is a phosphoramidite. The second reactive group can be a hydroxyl.

In one embodiment, the invention features a method of immobilizing a compound to a solid support. A compound having a reactive group is deposited onto a solid support having an immobilized functional group. The substrate is then contacted with an aerosol of an activator solution wherein the activator solution has an activator reagent dissolved in a solvent. Upon contact with the activator solution, the compound becomes attached to the substrate by coupling of the functional group with the activator group.

The method can further include immobilizing the compound where the compound is a solid. For example, the compound can be dry, i.e., not dissolved in solvent. One type of dry compound is provided in the form of a particulate composition. The compound can also be in the form of a thin film on the solid support.

The compound can be a nucleotide, an amine acid, or a small organic molecule.

The compound can further include a protecting group. For example, the compound can be a nucleotide with a protecting group attached to the C-3' or the C-5'. In another embodiment, the protecting group can be attached to an amino or carboxyl group of an amino acid. Further, the protecting group can be photosensitive, acid-sensitive, or base-sensitive.

In certain embodiments, the reactive group can be a phosphoramidite.

In certain embodiments, the functional group immobilized on the solid support can be a hydroxyl group.

The activator compound can be tetrazole, 5-(p-nitrophenyl)-1H-tetrazole, 5-ethylthio-1H-tetrazole, 4,5-dichloroimidazole, benzimidazolium triflate, or 4,5 dicyanoimidazole. The concentration of the activator compound can be between 0.1M and 1.0M, e.g., 0.2M to 0.8M or 0.2M to 0.6M. The activator compound can be dissolved in a high boiling point solvent, or a liquid composition that includes a high boiling point solvent and a low boiling point solvent.

The invention can also feature reacting unreacted immobilized functional groups with a capping reagent. For example, the unreacted functional groups can be treated with an acylating agent such as acetic anhydride.

In another embodiment, the invention features a method of forming an array of compounds. The method includes immobilizing a dry compound having a reactive group onto a solid support, wherein the solid support has attached functional groups. An organic solution of activator compound is then dispensed onto the solid support. This immobilizes the compound to the solid support by coupling the reactive group with the functional group. The uncoupled functional groups are then reacted with a capping reagent.

The invention further features a method of coupling compounds by generating an aerosol of activating compound and contacting it with a functional group and a dry composition that includes a protecting group and an activating group. This causes coupling of the dry composition to the functional group.

The method can further include generating the aerosol using positive pressure. The aerosol can also be generated from a spray head connected to pressurized nitrogen. Additionally, the aerosol can be generated into atmospheric conditions or non-atmospheric conditions.

In another embodiment, the invention features a method providing a solid support having a substrate with functional groups attached. Dry thin films of compounds having a reactive group and a protecting group are formed onto the solid support. The solid support is then contacted with an aerosol of organic solvent, the solvent having an activator compound dissolved therein. This immobilizes the compound to the substrate by coupling the reactive group with the functional group. The unreacted substrate is then reacted with a capping reagent, and the protecting groups are subsequently removed. In another embodiment, the method can be performed, repeating as many times as desired, the steps from forming dry films of compounds onto the solid support to removing the protecting groups.

The invention also features an apparatus. The apparatus includes applicator units, each unit including a dispenser that deposits compounds onto a solid surface, a reservoir for storing an organic solution comprising an activating reagent, and a spray head in fluid connection with the reservoir and adapted to create an aerosol of the organic solution. The apparatus can include an actuator that actuates the solid surface from the applicator units to a position to receive the aerosol from the spray head. The applicator units can each apply a different monomer, e.g., a nucleotide dissolved in a low boiling point solvent.

The apparatus can further include an applicator for capping unreacted portions of solid support, wherein the applicator deposits the capping reagent onto the solid support.

The apparatus can further include a housing adapted to provide a dry atmospheric environment.

In another embodiment, the invention features a method of forming an array. The method includes: providing a planar solid support that has a reactive surface; patterning each of a plurality of selective regions of the solid support with a compound; covalently bonding the compound to the support; and capping unpatterned regions of the support with an protecting group, whereby the capping defines the shape of the regions of compound on the solid support. The method is used during the formation of the first layer of the array, e.g., to pattern it for subsequent layers. The planar solid support can have a uniform reactive surface when provided. The compound can differ between selective regions of the plurality.

In the context of this invention, the following terms are defined: "Dry" means solid phase at a given time, i.e. not dissolved in an aqueous or organic solution. For example, a dry film of a nucleotide can be made by applying a nucleotide dissolved in acetonitrile and evaporating the acetonitrile. "Aerosol" means a fine mist of a liquid. "Low boiling point solvent" means a solvent having a boiling point of 85° C. or less at atmospheric pressure. A "high boiling point solvent" refers to a solvent that has a boiling point of greater than 85° C. at atmospheric pressure.

In another aspect, the invention features a method that includes forming a patterned deposition of a compound on a first substrate; positioning the first substrate in apposition to a second substrate; and transferring at least a portion of the dry deposition from the first substrate to the second substrate to produce a patterned dry deposition of the nucleotide on the second substrate. The patterned deposition can be a dry deposition, e.g., a deposition of particles (e.g., particles described herein, such as nucleotide particles) or a thin film (e.g., a thin film described herein). In one embodiment, the dry deposition includes particles that include a nucleotide, e.g., a charged nucleotide. The nucleotide can include a 5' or 3' protecting group and/or an activated group, e.g., a phosphoramidite.

The first substrate include sections that include depositions of a first nucleotide and other sections that include depositions of a second nucleotide, e.g., at least a section for each of at least four nucleotides.

The transferring can include applying an electrical field, e.g., generating a plasma of ions. The electric field can have a voltage of between 500 and 50,000 V, 3000 and 12000 V, or 4,000 and 8,000 V. The electrical field and/or ionized atoms can be generated by a field generator such as a corotron or scorotron. The second substrate can be grounded. A field generator can be scanned across the first substrate while it is apposition to the second substrate. In one embodiment, there is no physical contact between the first and second substrate, e.g., there is a gap. The gap can be at least partially under vacuum.

In one embodiment, the first substrate is flexible, e.g., paper or a transparency or transparency-like surface. The second substrate can be rigid. The positioning can include aligning the first and second substrate The method can include coupling the nucleotide to the second substrate, e.g., by applying an activator compound, e.g., as described herein. The method can further include repeating the forming, positioning, transferring, and coupling for each register of the nucleic acids to be synthesized.

In another aspect, the invention features a method of providing an array of chemical compounds. The method includes providing a plurality of interim substrates. Each interim substrate includes a different particles of a component of a complex chemical compound. The particles are disposed at different addresses of the interim substrate. The method also includes sequentially, for each interim substrate of the plurality of interim substrates, transferring the particles from the different addresses of the interim substrate to corresponding addresses on a target substrate, and coupling the components to the target substrate to form a nucleic acid at each of the different addresses of the target substrate. In the cases in which at least some of the particles include a nucleotide, the method can be used to provide an array of nucleic acids.

In another aspect, the invention features an apparatus that includes a first substrate, a second substrate, and an electrical field generator. The first substrate includes dry depositions of polymer subunits. Each deposition is at a predefined address such that different polymer subunits are selectively positions at different addresses on the first substrate. The first substrate can be, e.g., flexible, e.g., paper or a transparency. The second substrate can be flexible or rigid, and optionally transparent, e.g., glass. The first and second substrate are positioned in apposition to each other. In one embodiment, the second substrate is grounded. The electrical field generator can be, e.g., a corotron or a scorotron. The generator can be attached to a guide or translator which can translate the generator across the first substrate.

In still another aspect, the invention features an article that includes a machine-readable medium that stores machine-executable instruction. The instructions cause a machine (e.g., a processor) to (1) store biopolymer sequences, each of the sequences being associated with a two-dimensional address on a substrate; (2) generate layer maps, wherein each of the layer map corresponds a position in at least a subset of the biopolymer sequences and assigns monomer identities to at least a subset of addresses of the substrate; and sequentially for each of the layer maps, and (3) process (e.g., rasterize) the layer map to generate triggers for each of the photoreceptors such that the triggers selectively illuminate regions of the photoreceptor, each region corresponding to an address of the substrate, the regions being illuminated only if the corresponding address is assigned to the monomer for which the photoreceptor is configured. The machine can interface with the charge pattern generators, e.g., the light emitters of the charge pattern generators, to selectively trigger the light emitters to illuminate regions of the photoreceptor. The instructions can further cause the machine to send the triggers to appropriate applicator units.

The instructions can include detecting signals from an apparatus to synchronize the position of a substrate along a substrate path with a photoreceptor. The instructions can also include accepting input from a user, the input indicating the size of each address on the substrate. Other inputs include identifiers and/or sequences of the biopolymers to be synthesized.

Aspects and details of the features described above can be combined in numerous ways as apparent to the skilled artisan and from the detailed description below.

The methods, compositions, apparati, and systems described here provide a method for the fabrication of arrays of biopolymers in large numbers, in many varieties, at high speed, with great precision and low cost. Notably, in embodiments using a software controller to direct deposition of chemical monomers, considerably versatility is achieved, as features of the array can be sized and resized based on software commands without any change or adaptation of an apparatus or composition. Thus, for example, the same instrument can be used to fabricate dense arrays with numerous features (e.g., for high-throughput applications) as well as sparse arrays having large features (e.g., for detailed studies that required increased accuracy and reproducibility).

Many aspects of this disclosure are suited for the challenges of industrial-scale production of oligonucleotide arrays. For example, (a) they facilitate: high synthetic yield at each coupling step; (b) they are spatially addressable on the substrate; (c) they are flexible in their adaptation of a configuration of any specified set of sequences in any pattern; (d) they are amenable to mass production. The methods also do not require the usage of a photomask or a chemical mask layer, e.g., an epoxy, lacquer, or oil mask that is stripped and reapplied between additions of different compound. Chemical activation of coupling avoids the use of heat which is generally harsher and less energy efficient.

The details of one or more embodiments of the invention are set forth in the description below. Other features, objects, and advantages of the invention will be apparent from the description and from the claims.

DETAILED DESCRIPTION

An array of chemical compounds can be produced by the electrostatic deposition of its components onto a substrate.

The subunit are coupled to the chemical groups on the substrate to synthesize a complex compound. By localizing the electrostatic deposition, different building blocks can be coupled at different positions on the substrate. Thus, a diverse and addressable set of chemical compounds is produced on the substrate to form an array of chemical compounds, e.g., of biological polymers. One application of this concept is the production of an oligonucleotide array. Other concepts provided here can be used in combination with the electrostatic deposition method or with other chemical synthetic methods.

The electrostatic deposition of chemical subunits, at least in some respects, includes features of electrophotography. Electrophotography is a complex process of printing images using light and the electrostatic force. In some implementations, it includes at least six processes: charging a photoreceptor, expose to light to form latent image, toner development, transfer of imaged toner, fusing of the transferred toner and cleaning of the photoreceptor. Xerography (meaning, "dry writing" in Greek), is one common application of electrophotography, widely used in paper copiers and printers to produce high quality images (see, e.g., "Xerography" by Dan A. Hays, Encyclopedia of Applied Physics, American Institute of Physics, Vol. 23, 541–561, (1998) and "Physics of Electrophotography", by Damodar M. Pai and B. E. Springett, in Review of Modern Physics, Vol. 65, No. 1, January (1993)).

As disclosed in U.S. Pat. No. 2,297,691, photoconductive materials are charged in the dark and then exposed to patterned light in the form of a projected image to produce an electrostatic image which is then developed using a charged pigmented powder, often referred to as a toner. A review of the xerographic technology is provided in "The Physics & Technology of Xerographic Processes," by E. M. Williams, (1984), and "Electrography and Development Physics," by L. B. Schein, (1988).

Figure 1:
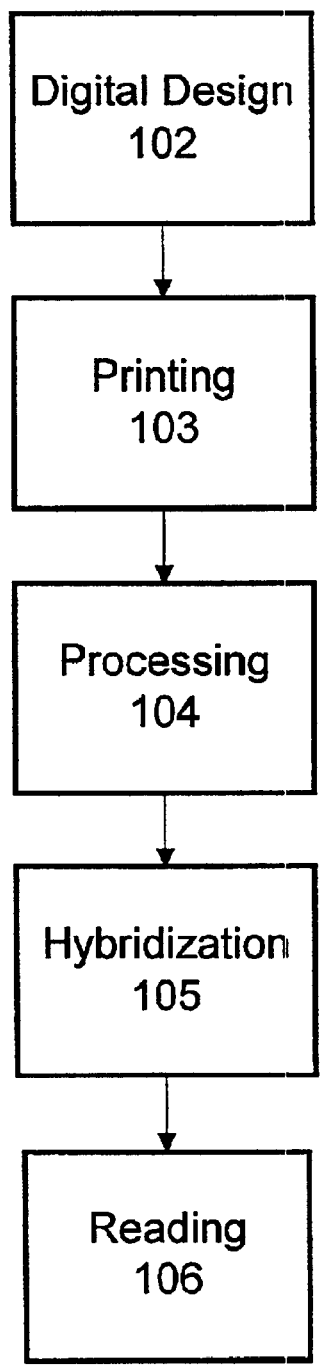
FIGS. 1, 2, 4, and 19 are flowcharts of exemplary processes.

Referring to the exemplary process shown in FIG. 1, oligonucleotide array construction includes the digital design 102 of the array, printing 103 the array, post-processing 104 of the printed arrays, hybridization 105 of a sample to the array, and reading 106 the array.

Figure 18:
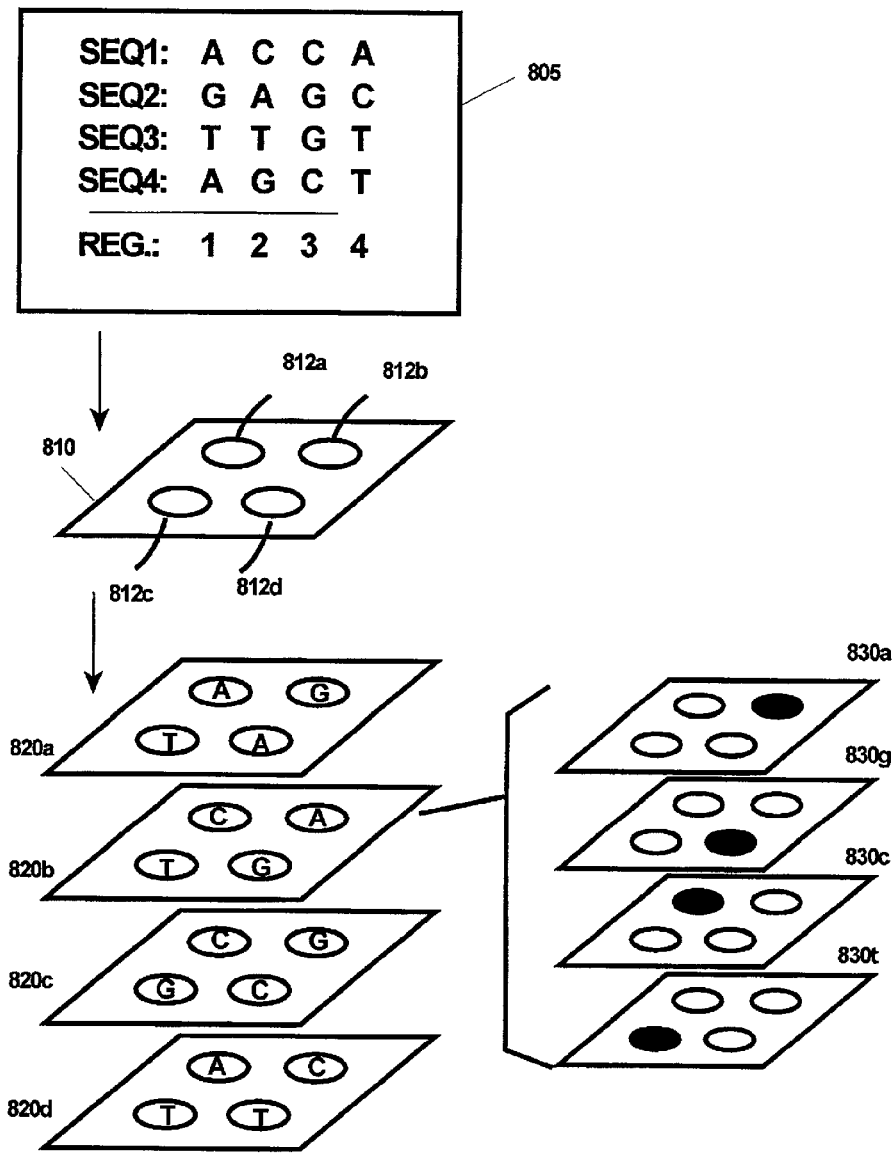
FIG. 18 is a schematic of an exemplary process for image map construction.

The digital design 102 includes the patterning a two-dimensional map with unique positional addresses. The digital design process is also described below (see "Digital Design"). Each address is assigned a nucleic acid sequence. Typically, different sequences are positioned at different addresses, although some may be duplicated to provide controls and verification. Referring to FIG. 18, the digital design process translates the set 801 of strings representing the nucleic acid sequences into a series of layer maps, 820a, 820b, 820c, 820d, each layer indicating a nucleotide monomer to be added at a given register. A layer map includes information for four different image maps, 830a, 830g, 830c, 830t, one for each nucleotide (A, G, C, T). Each image map indicates, typically in a binary fashion, whether the given nucleotide is to be added to an address. Thus, a layer map for adenine indicates addresses where an adenine nucleotide is to be coupled to a growing chain. Each nucleotide image maps is interpreted during the printing 103, e.g., to control the spatial position of electrostatic deposition of nucleotide monomer subunits, e.g., as described below.

It is also possible stagger the registers, e.g., by not adding a monomer for some addresses in a particular layer map, and it is possible to include information for additional image maps, e.g., for unnatural nucleotides or other chemical compounds to be added. Similarly, if the nucleic acids being synthesized are of different lengths, some addresses may not be indicated for nucleotide deposition in at least one of the layer maps.

Figure 2:
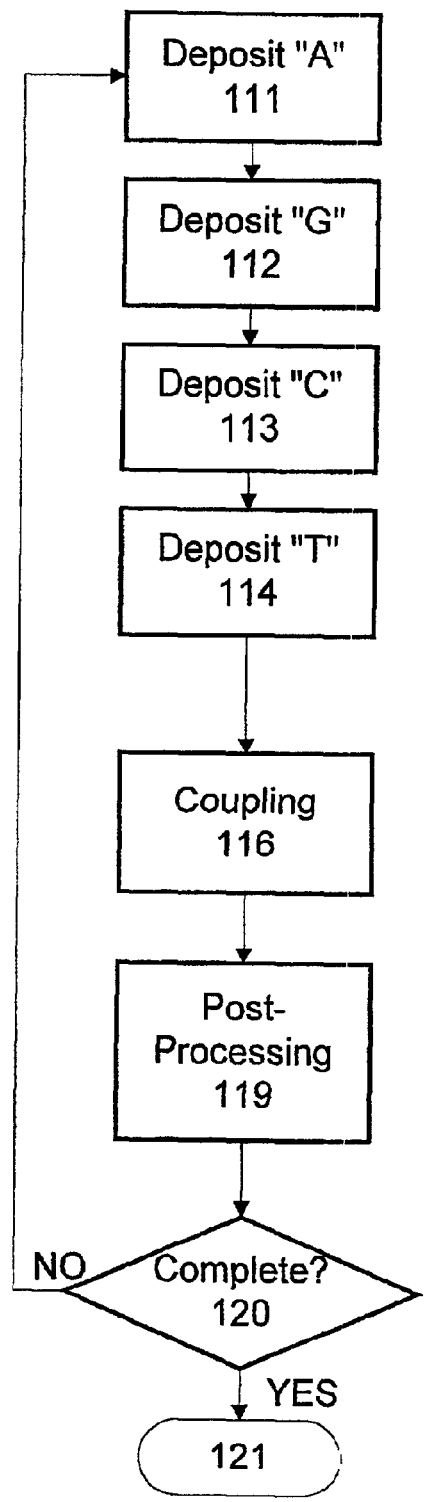
Figure 3:
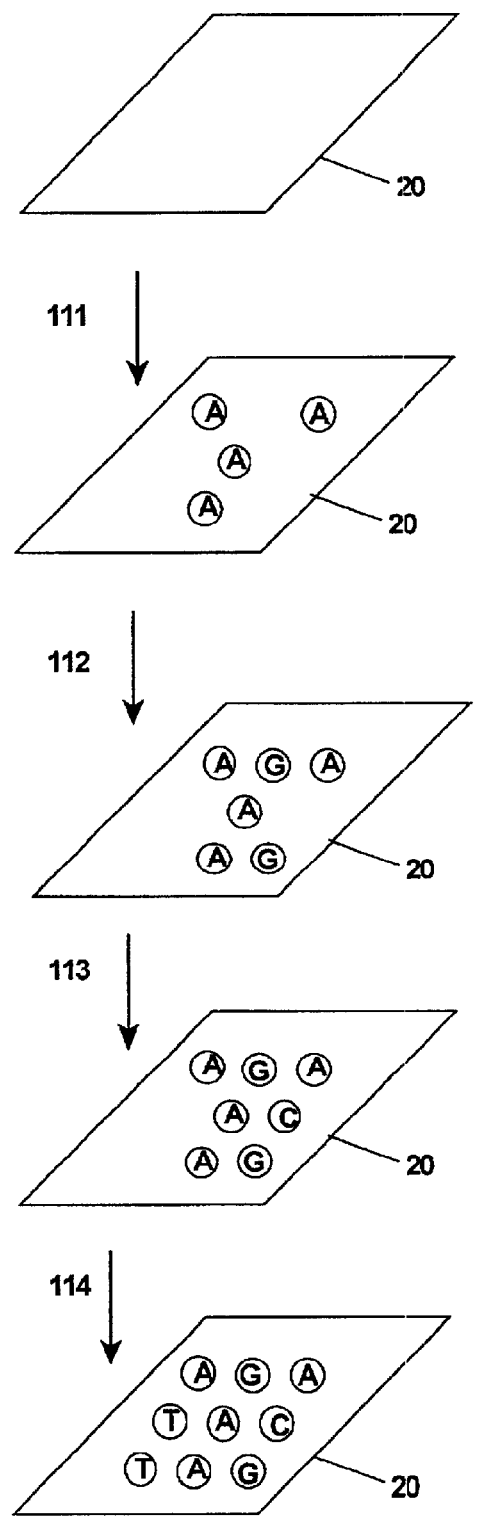
FIG. 3 is a schematic of an exemplary nucleotide printing process.

Referring to FIGS. 2 and 3, a first exemplary implementation of the printing process 103 includes cyclically depositing the four canonical nucleotide compounds 111, 112, 113, 114 onto a substrate 20, and coupling 116 the depositing nucleotide molecules to a reactive end of a growing chain on the substrate 20. The deposition of the four different nucleotides typically occurs sequentially. Four applicator units are used, each is dedicated to the printing of one of the canonical deoxyribonucleotides (A, G, C, T). Spatial information, e.g., in the form of an image map (see below), indicates to each applicator unit regions of the substrate 20 where the nucleotide compounds is to be applied. The substrate is post-processed 117 for chemical modification. After one cycle, the process is repeated 120 until all the nucleic acids are synthesized.

Figure 4:
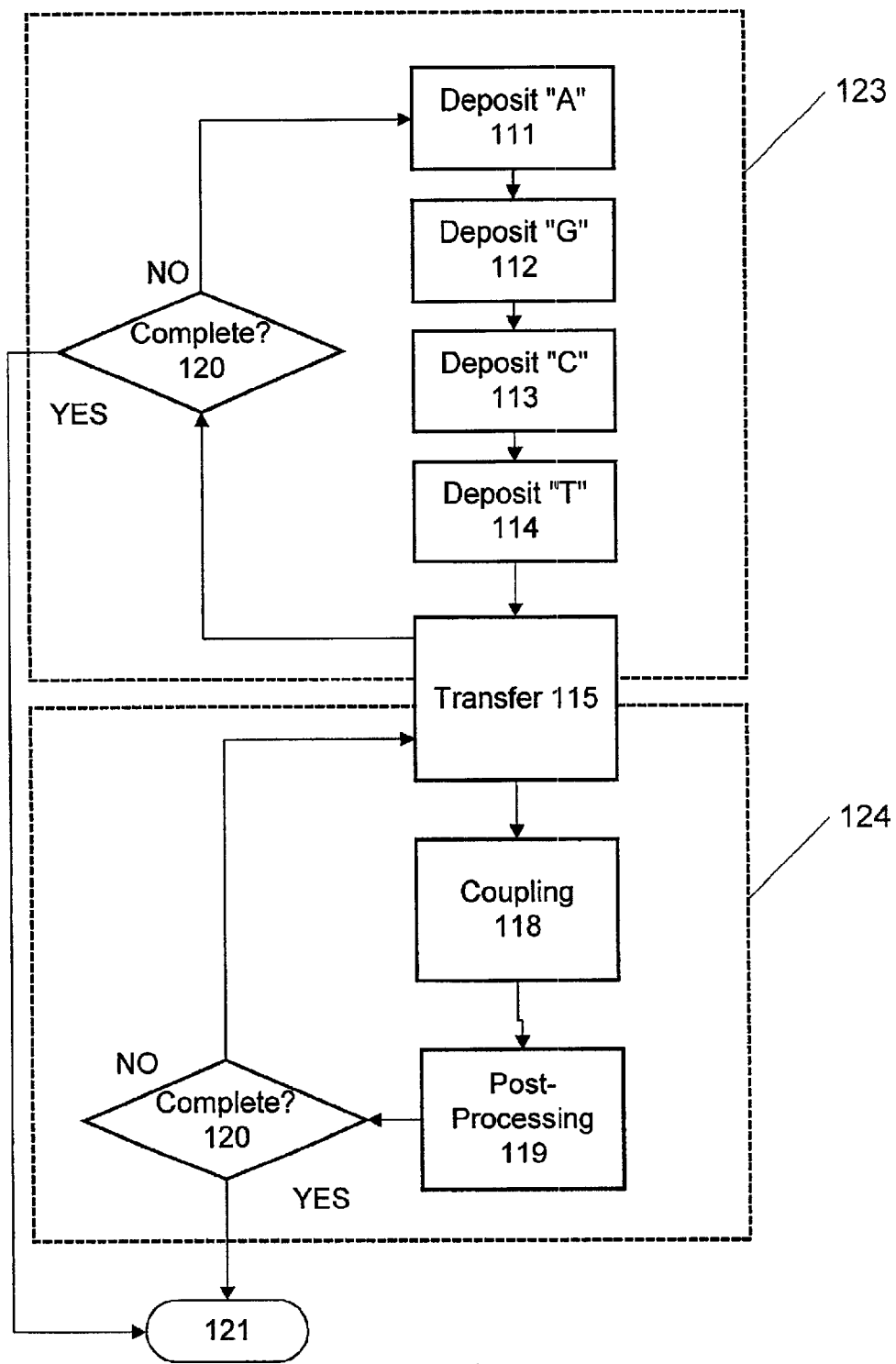

Referring to FIG. 4, a second exemplary implementation of the printing process 103 includes: two cycles 123, 124. The cycle 123 results in the printing of interim substrates whereas the cycle 124 results in the synthesis of polymers on the target substrate. The cycle 123 includes cyclically depositing nucleotide particles using four applicator units 111, 112, 113, 114 onto an interim substrate, and transferring 115 the particles from the interim substrate to a target substrate. The cycle 124 includes, after the transfer process 115, coupling 116 the transferred nucleotide molecules to a reactive end of a growing chain on the target substrate, and post-processing 119 the target substrate. After one cycle, the process is repeated 120 until all the nucleic acids are synthesized.

In the embodiment shown in FIG. 4, the cycles 123 of interim substrate printing are synchronized with the synthetic cycles 124 of the target substrate. In this case, an interim substrate is not printed until the deposits on a previous interim substrate have been transferred to the target substrate. In another embodiment (not shown in FIG. 4), the cycles 123 of interim substrate printing are decoupled from the synthetic cycles 124 of the target substrate. In one example, all the interim substrates are printed, i.e., one for each layer. After completion 121 of the interim substrate printing cycles 123, the interim substrates are sequentially transferred to the target substrate. Other examples can include varying degrees of temporal coupling between the cycles 123 and 124.

Toner Preparations

Figure 13:
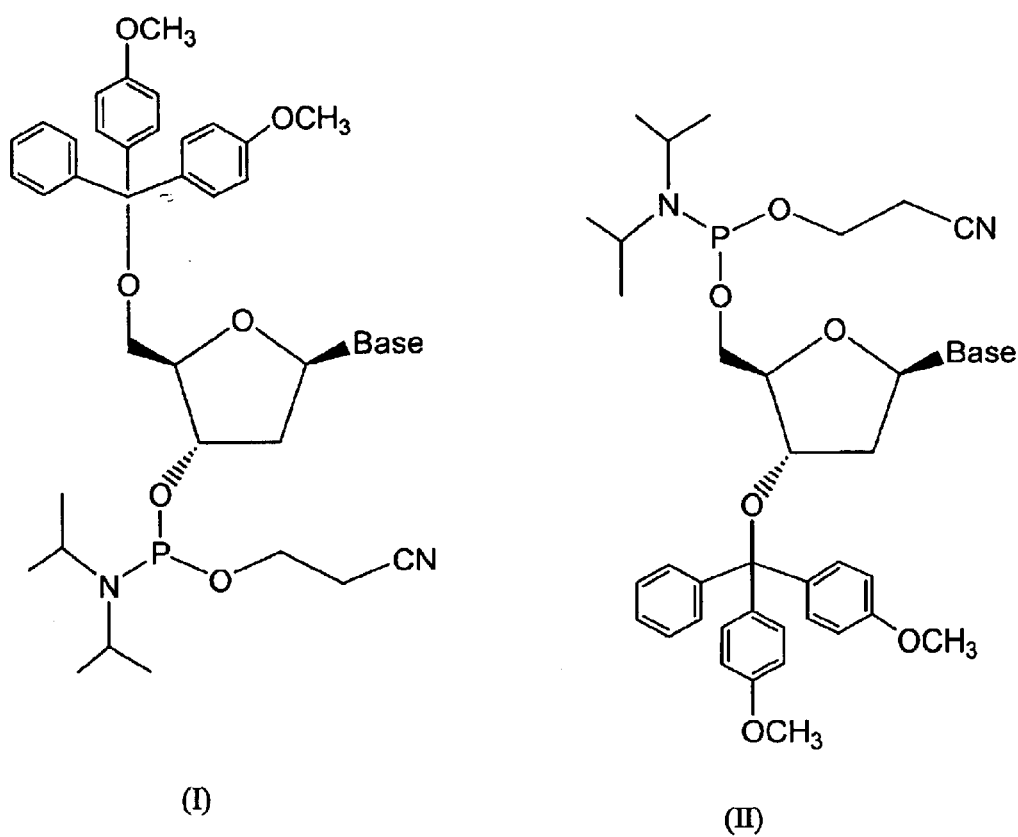
FIG. 13 depicts the chemical structure of exemplary nucleotide monomers.

For electrostatic deposition, particles of polymer subunits are charged and then bound to a patterned region on the surface of a photoreceptor. When the polymer subunits are nucleotides, the particles can be composed of nucleotides that are protected on one terminus, and activated on the other. (The terminus refers to the nucleotide C-5' or C-3' position.) Exemplary nucleotide compounds I, II are diagramed in FIG. 13. Compound I has a 3' phosphoramidite and a 5' protecting group. Compound II has a 5' phosphoramidite and a 3' protecting group. In still other examples, e.g., following the synthetic process described in U.S. Patent application Publication US2001/0044530, published Nov. 22, 2001, the compound includes a protecting group, but not the phosphoramidite. In this case, the substrate to which the nucleotide is coupled can be modified with a phosphorous activating group such as a phosphoramidite. Other nucleotide coupling chemistries can be used, e.g., phosphodiester or phosphotriester. Both dry and liquid toners that include the nucleotide particles can be prepared.

Nucleotide particles are produced from powders of amorphous nucleotide subunits (e.g., phosphoramidite nucleotides). The powders are processed (e.g., by jet milling) to produce particles. The particles are typically less than 100, 50, 30, 20, 18, 15, 12, 10, 9, 8, 7, or 6 μm in diameter, e.g., on average about 7 μm in diameter. For example, after jet milling, the particles can be sorted by a classifier into desired size ranges, e.g. less than about 30, 20, 10, or 5 microns in diameter.

The nucleotide particles are can be combined with other additives to prepare a nucleotide toner preparation. The toner preparation is then mixed with a carrier preparation that includes carrier beads that include a metal oxide, e.g., ferrite carrier beads. One available carrier bead is the Powdertech carrier DM070C silicone coated ferrite. This combination, referred to as a developer composition, is then triboelectrically charged. The carrier beads can be about, e.g., 30 to 80 μm in diameter. In some cases, they are larger in diameter than the nucleotide particles. The charge characteristics, Q/M (charge over mass ratio) are measured with a charge spectrometer such as the "q-test" equipment made by Epping GmbH, Germany and/or Q/M meter (Model 210HS, Trek Inc., NY). It has been found that nucleotide particles of less than 50 μm diameter are chargeable to an absolute value of at least between 5 and 50 μC/g.

In the presence of carrier beads, the nucleotides particles, absent other components, can acquire a high charge which is unstable. While such particles are usable, it is also possible to prepare particles that can be charged in a more stable manner as it is particularly useful if the charge is stable over time, e.g., throughout multiple printing runs. The charging properties of the particles can be controlled by the addition of a surface charge control agent.

A surface charge control agent is an agent that has one or more of the following functions: stabilizing charge on the nucleotide particles, distributing charge between nucleotide particles and other particles, and determining polarity of the charge on the nucleotide particles.

By using certain surface charge control agents, the nucleotide particles are positively charge during the mixing. Other surface charge control agents can be used to negatively charge the particles. The printing apparatus is configured according to the polarity of the charge on the nucleotide particles.

Figure 5:
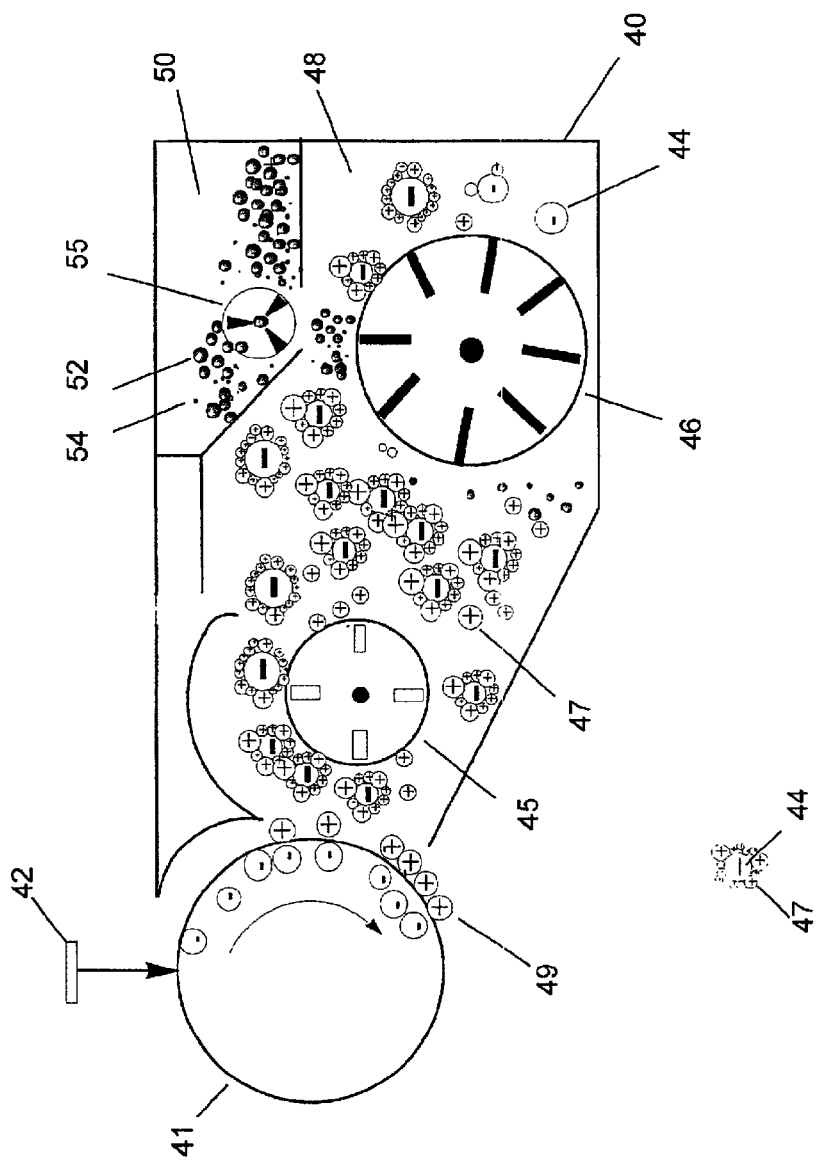
FIGS. 5 and 6 are schematics of an exemplary unit for charging nucleotide particles.

Referring to FIG. 5, an applicator unit is used to triboelectrically charge a toner composition and selectively bind it to a photoreceptor 41. The toner composition, which includes nucleotide particles 52 (initially uncharged) and surface charge control agents 51, is dispense from the reservoir 50 into the chamber 48. In the chamber 48 it is mixed with ferrite carrier beads 44. Rotating magnetic brushes in the chamber 45, 46 agitate the mixture. Contact between the carrier beads 44 and the nucleotide particles 47 results in triboelectric charging of both. As shown in this example, the nucleotide particles are positively charged. In the vicinity of the photoreceptor 41, the positively charged nucleotide particles 47 are attached to regions on the photoreceptor surface that are not positively charged. These regions 49 were created by selectively illuminating the photoreceptor 41 using a light source 42. See, FIG. 7 and its description for additional detail.

Figure 6:
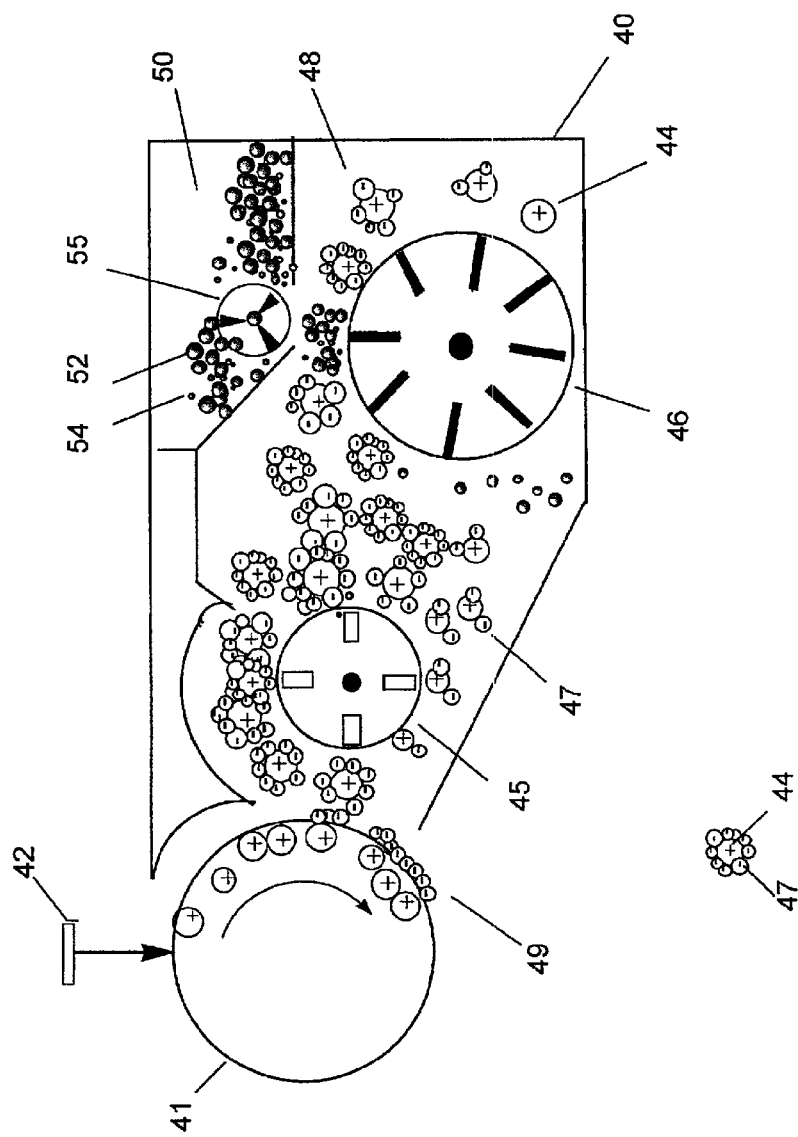

Similarly in FIG. 6, the toner composition becomes negatively charged. Carrier beads that favor negative charging are combined with the nucleotide particles and tested as described below. Beads can be obtained from Powdertech (Chiba-Ken 277-0872 Japan).

Examples of surface control agents that stabilize the nucleotide particles (e.g., the charge and/or structural property of the nucleotide particles) include: polystyrene, polyformaldehyde, polymethylmethacrylate, polyamide, fumed silica, amorphous silica, polyethylene glycol succinate, polyethylene glycol adipate, polydiallyl phthalate, polyurethane elastomer, styrene-acrylonitrile copolymer, styrene-butadiene copolymer, polyisobutylene, borosilicate glass, polyethylene glycol terephthalate, epoxide resin, polychlorobutadiene, butadiene-acrylonitrile copolymer, polyacrylonitrile, polyethylene, chlorinated polyether, polytrifluorochloroethylene and polytetrafluoroethylene.

By adding surface charge control agents such as cabosil, a fumed silica, and Kynar, a highly fluorinated polymeric material, the charge stability of some nucleotide particles was maintained. Polystyrene improved the triboelectrification with the ferrite carrier beads. Lubricants (such as zinesteric) can also be added.

Carrier coating materials can also influence the characteristics of the developer preparation. Examples of such materials include the triboelectric series which includes kynar (polyvinylidene fluoride), Saran F220 (vinylidene chloride-acrylonitrile copolymer), polysulfone, Cyclolac H-1000 (acrylonitrile-butadiene-styrene terpolymer), polyethylene, polystyrene, polyurethane, alkyl-substituted polyvinyl pyrrolidone, diallyl phthalate and methyl methacrylate (see, e.g., U.S. Pat. No. 3,795,617).

One general method for preparing a nucleotide toner is to screen different components mixed with the nucleotide particles for the ability of the combination to function as a toner. Among the parameters that can be varied are the nucleotide particle concentration (e.g., about 2 to 99.9% pure nucleotides), the surface charge control agent and its relative concentration, and other additives selected from the triboelectric series (see, e.g., Henniker, (1962) Nature, 196, 474). Different combinations, ratios, and agents can be tested, e.g., systematically. The screening process can include measuring the Q/M parameter and then a trial electrophotographic transfer. These tests can be performed with or without carrier beads. Further adaptation of a toner composition can include monitoring the number of particle size distribution and charging properties after multiple rounds of printing. Structurally durable compositions are able to withstand many such cycles without deterioration in particle size or charging property.

The chemical synthetic processes described here can also use liquid toners compositions. Liquid toners can include submicron-sized toner particles are dispersed in a dielectric liquid. These nucleotide particles are can be, e.g., between 50 Å and 30 μm, 100 Å and 5 μm, 50 Å and 1 μm in diameter, on average. The liquid toner is applied to the photoreceptor and the toner particles, attracted by the electric field of the latent image, electrophoretically migrate to the photoreceptor (see, e.g., Clause and. Mayer: in *Xerography and Related Processes*, ed. Dessauer and Clark (Focal, New York 1965), Chapter 12). This electrophoretic property is helpful for focusing the particles on the latent image and, for at least this reason, is suited for high-density arrays.

The charging behavior of the nucleotide particles in a liquid medium may be defined by the zeta potential, which is the potential difference between the charge on the particle and the countercharge in the liquid. The electrophoretic mobility of the particles is proportional to the zeta potential. In some implementations the absolute value of the zeta potential is about 35, 40, 50, or 60 mV.

The liquid medium can have a high volume resistivity (e.g., at least $10^8$, $10^9$, or $10^{10}$ Ωcm, and optionally between $10^8$ and $10^{12}$, or $10^9$ and $10^{11}$) so that it will not destroy the latent image on the photoreceptor. The liquid medium can be a chemically inert, non-dissolving organic solvent, e.g., a high molecular weight aliphatic hydrocarbon based solvent, such as an isoparaffin e.g., Isopar® C (and related products from ExxonMobil Chemical) (2,2,4 trimethylpentane).

The dry toner compositions can be a mixture, e.g., of the different components described above, or, in some embodiments, it can be prepared as a composite. An example of the preparation of a dry toner composition is provided below.

Amino acid toners can also be made, e.g., following these methods.

Figure 16:
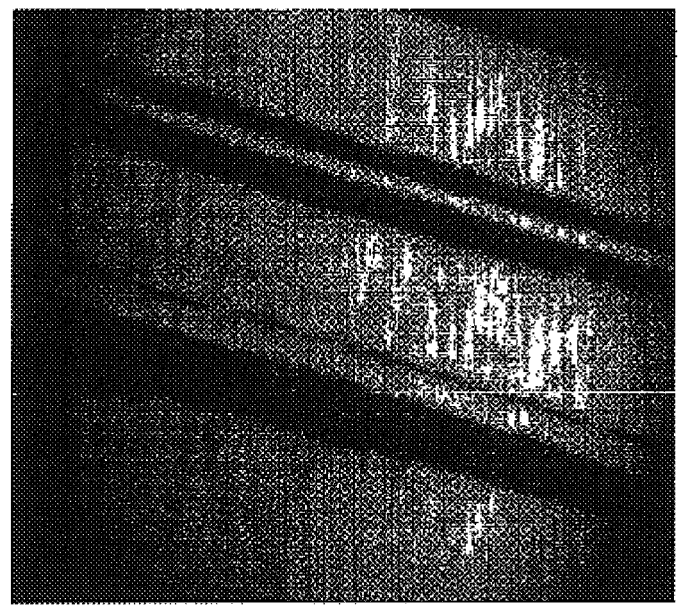

FIG. 16 is an image of the successful electrostatic transfer of nucleotide particles from a liquid toner composition that included nucleotide particles suspended in Isopar® (available from Exxon Mobil Corp.). Liquid nucleotide toners are useful for the production of high density arrays.

Liquid and dry toner compositions can be distributed to users in containers that include nucleotide toner particles. In addition to distributing the nucleotide particles alone, the compositions can also be distributed as mixtures that include one or more other components, e.g., one or more of a surface charge control agent, carrier bead, lubricant, and so forth. The toner particles in the packages can be chargeable, but may not necessarily be charged at a given time. These packages can be used to replenish toner for a nucleic acid printing apparatus, e.g., an apparatus described herein.

Electrophotographic Printing

Figure 7:
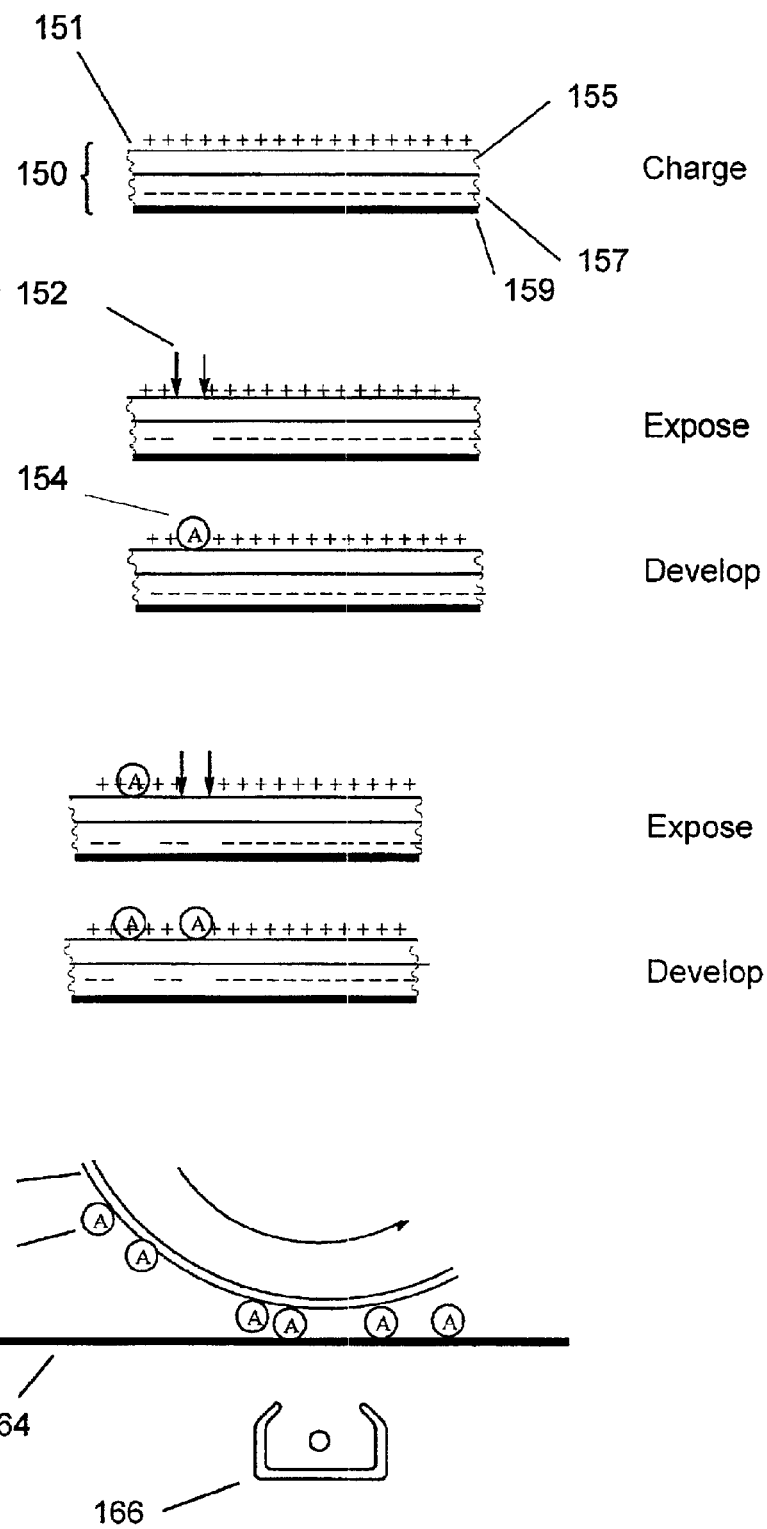
FIG. 7 is a schematic of an exemplary process for electrostatic deposition using a photoreceptor.

Referring to the example in FIG. 7, a photoreceptor 150, located within an applicator unit, is used to selectively deposit charged nucleotide particles using the electrostatic force. Of course, any selectively chargeable surface can be used to deposit the charged nucleotide particles.

The photoreceptor surface 151 is first charged so that it has the same charge as the nucleotide particles. In this example, the surface and the particles are positively charged. The photoreceptor surface 151 can be charged, e.g., using a corotron or a scorotron.

After the photoreceptor is fully charged, it is selectively illuminated, e.g., by a scanning modulated laser or an array of light emitting diodes (LEDs). The illumination is controlled by the digitized pixel information provided by the image maps. Illumination decharges the selected regions on the photoreceptor. When the decharged region of the photoreceptor passes through the loading zone where the triboelectrically charged nucleotide developer composition resides, the positively nucleotide particles are electrostatically attracted to the exposed portions on the photoreceptor. As a result of rotation, the photoreceptor drum or belt advances, moving another position under the illumination source and the position bound by the nucleotide particles into a transfer zone where the particles are transferred to a substrate 164. An electrical field, e.g., provided by a corona 166, facilitates the transfer to the substrate 164.

The photoreceptor can be, for example, a drum (see, e.g., FIG. 10) or a belt (see, e.g., FIG. 9) stretched across drive and belt support rollers.

Figure 8:
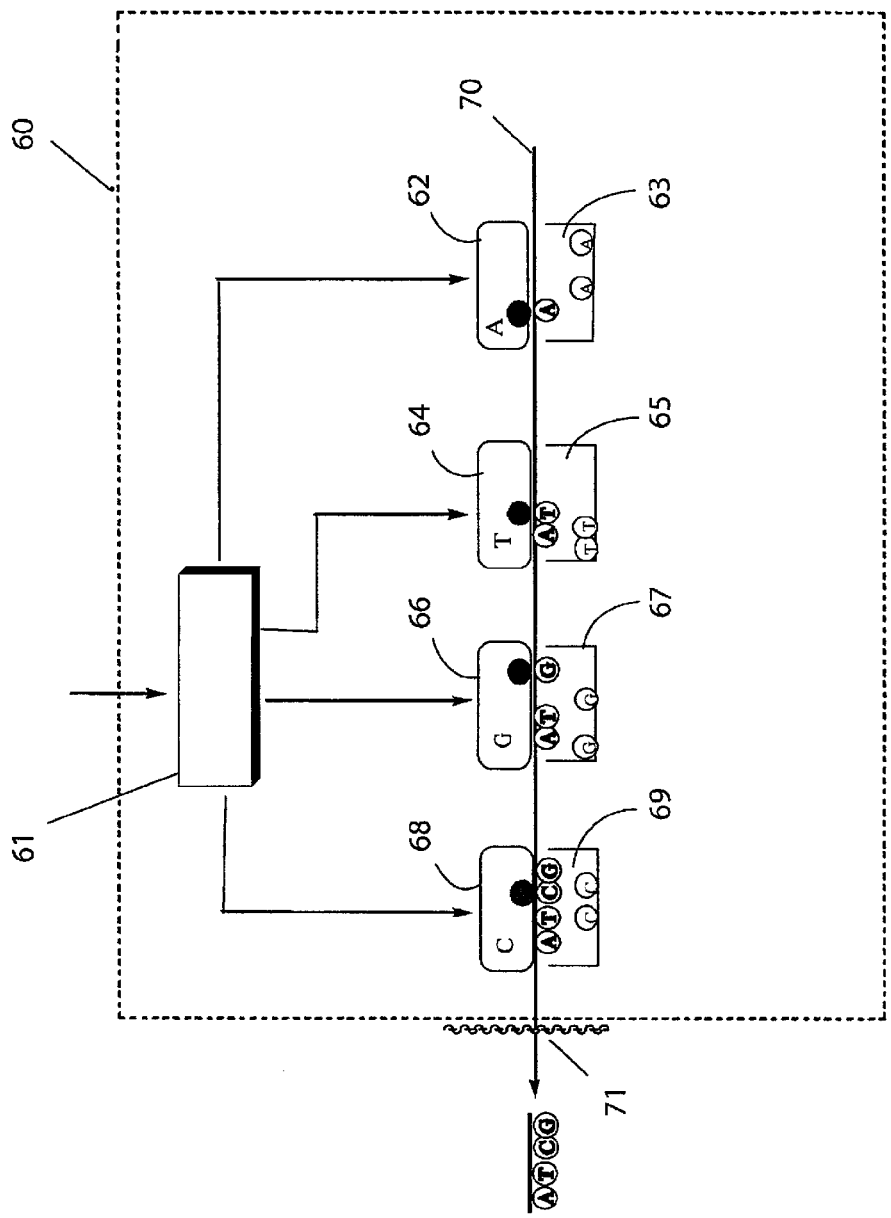
FIGS. 8, 9, and 10 are schematics of exemplary apparati for printing nucleotide particles.

Referring to FIG. 8, typically at least four applicator units are positioned in series along a single substrate path 70 so that each of the four canonical nucleotides can be printed onto the substrate. The four applicator units are controlled by a regulator 61 which can distribute image map information to each applicator unit and also synchronize the units so that that the four applicator units correctly reference each address on the substrate to prevent overlaps and other infidelities in printing.

The image development/transfer processes are conducted sequentially at each of at least four applicator units 62, 64, 66 and 68 using adenine phosphoramidite particles 63, thymidine phosphoramidite particles 65, guanosine phosphoramidite nucleotide particles 67 and cytidine phosphoramidite nucleotide particles 69 respectively. The four applicator units can be interfaced to each other, e.g., using the controller 61 which can provide synchronization signal, image maps and/or layer maps to the individual units. The substrate (e.g., an interim substrate or a target substrate) travels along the path 70 through the four developer/transfer stations 62, 64, 66, and 68. After the at least four subunits are printed, the substrate is processed 71, e.g., transferred to a target substrate in the case of an interim substrate, or treated for coupling of the subunits in the case of the target substrate itself.

A variety of different machine architectures can be used for producing the nucleotide image transfer by layers. The full layer of nucleotide image transfer can be accomplished in several ways. The four nucleotide images can be transferred sequentially to the substrate surface. They can also be accumulated on an intermediate roll or belt before transferring to the substrate surface. The images can also be accumulated on the photoreceptor and are then transferred to the substrate surface. In the latter design, the photoreceptor needs to be sequentially recharged, exposed and developed in the presence of previously applied nucleotide particles.

Figure 9:
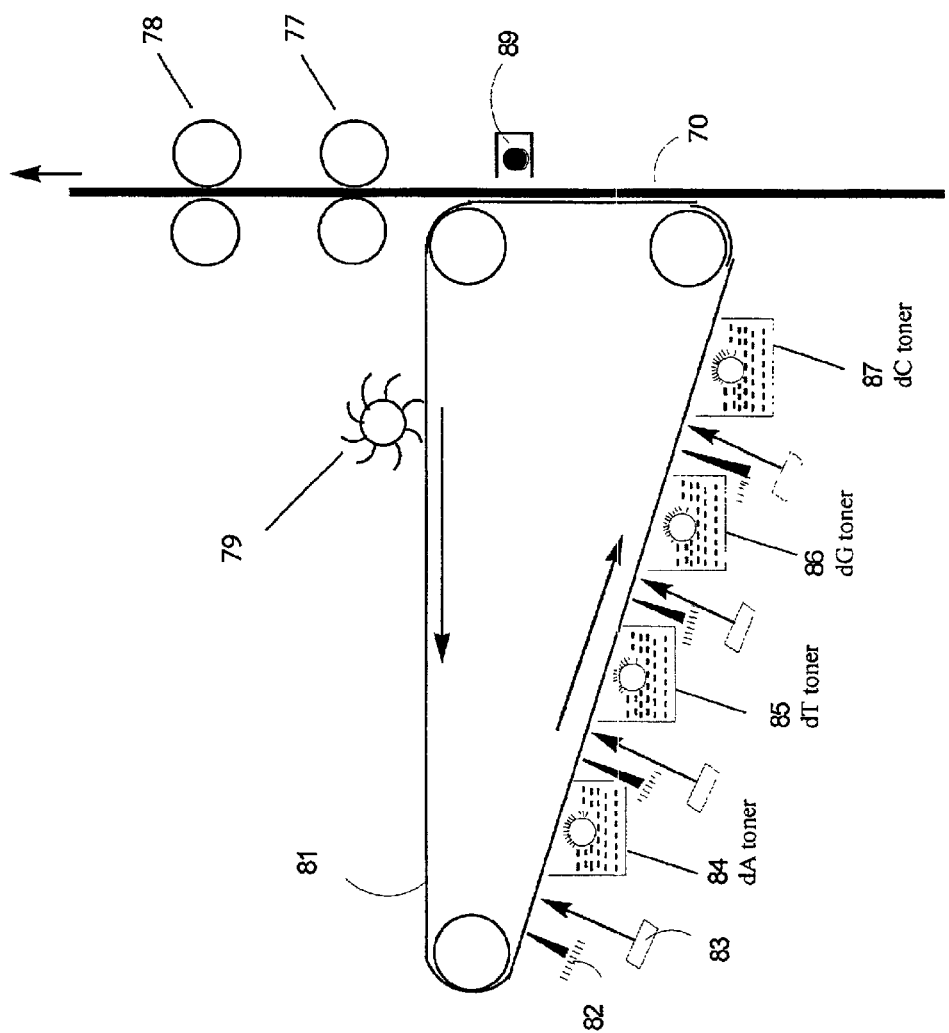
Figure 10:
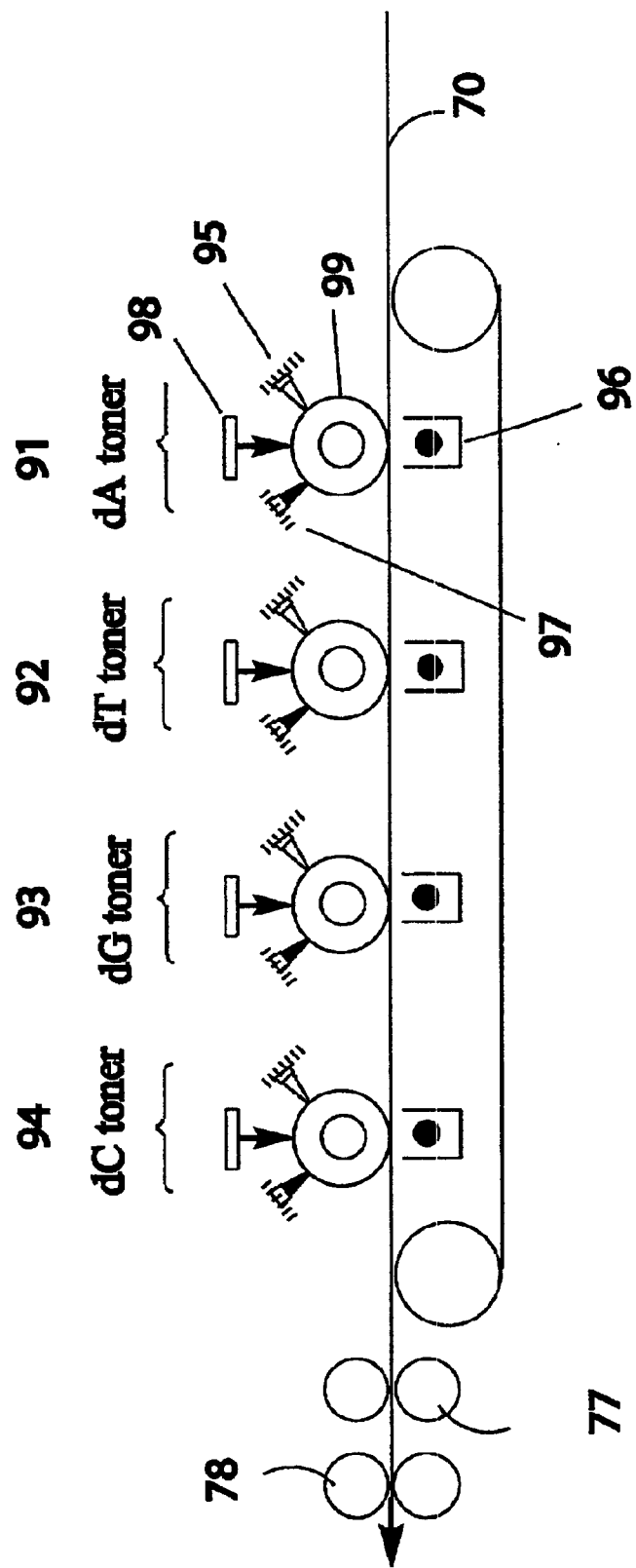

Referring to FIG. 9, an exemplary implementation is the Multiple Station Single Pass (MSSP) architecture. This apparatus produced am image by sequentially transferring adenosine 84, thymidine 85, guanosine 86 and cytidine phosphoramidite 87 toner images on to a belt photoreceptor 81. The rotating belt 81 is charged 82, exposed 83, and developed 84 for each nucleotide subunit. Transfer of the nucleotide particles on the belt 81 occurs after all four nucleotide subunit particles are accumulated on the belt. Transfer is effected in the transfer zone 89 where the full layer of the nucleotide image is electrostatically transferred to the substrate, e.g., using a corotron or scorotron.

An alternative MSSP system is shown in FIG. 9 where four separate applicator units, one each for adenosine 91, thymidine 92, guanosine 93 and cytidine phosphoramidite 94, are arranged in tandem. Each unit has its own photoreceptor 95, nucleotide particle loading zone 91, charging device 97, exposure 98 and the transfer 96. When the imaging substrate is in the form of sheets, a belt transports the sheet to each station where each different nucleoside powder image is transferred with a charge device. Each applicator unit can be interfaced to a common controller 61 (e.g., as shown in FIG. 8 and as described below) or to a computer system which provides image maps and/or layer maps to direct printing.

In other implementations, it is possible to generate a selectively charged surface without the use of light and/or a photoreceptor. Such a selectively charged surface can similarly be used to pattern nucleic acid subunits on a substrate.

Interim Substrate and Transfer

As seen above, one implementation features an interim substrate that receives particulate nucleotide compositions from applicator units by electrostatic deposition. The interim substrate can have the same properties as the target substrate (see "Target Substrates," below). Typically, the interim substrate is composed of a pliable material that can be rapidly fed and processed by a conventional xerographic device. It has been found that both paper and transparencies (transparencies for overhead projection of visual presentations such as are available from commercial suppliers such as 3M®. The interim substrate can be composed of, for example, Mylar™ (polyethylene terephthalate), polycarbonates, a nonvolatile organic acid selected from citric acid, and/or cellulose triacetate; polyvinylchlorides. It can include various coatings, including anti-static and/or hydrophilic coatings. For general guidance, see, e.g., U.S. Pat. Nos. 5,683,793; 5,672,424; 4,997,697; 4,956,225; and 5,897,540. For usage as an interim substrate, the "transparency" may either be transparent, partially-transparent or opaque.

Figure 14:
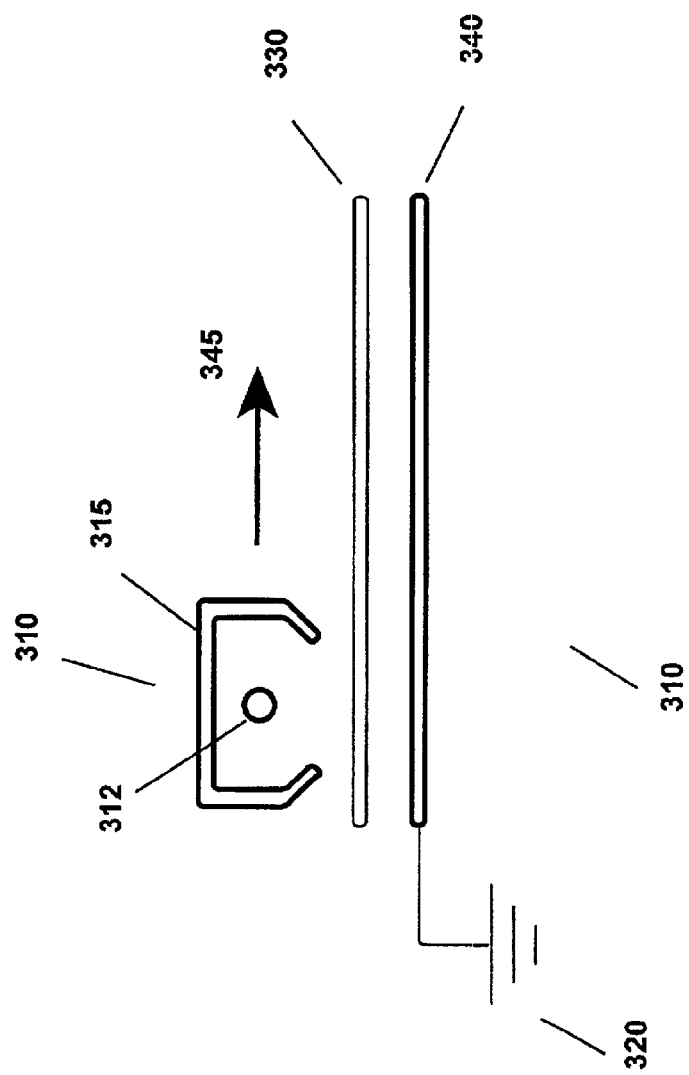
FIG. 14 is a schematic of an exemplary transfer device.

Referring to FIG. 14, nucleotide particles on the interim substrate 330 are transferred to the target substrate 340 using an electric field with a polarity that repels the charged nucleotide particles on the interim substrate 330. The electric field can be generated, for example, by a corotron, a scorotron, or a conducting roller.

The interim substrate 330 and the target substrate 340 are positioned in apposition to each other. There can be a gap between the two. The target substrate is grounded. Then, as shown in FIG. 14, a corotron 310, which includes a ground shield 315 and a thin wire (e.g., <100 μm in diameter) 312, is scanned 345 across the interim substrate 330 while a high DC voltage (e.g., between 1000 to 10000 V-DC, e.g., about 5000 to 8000 V-DC) is applied to the wire. The corotron generates ions of the same polarity as the wire. These ions are swept by the electric field towards the interim substrate 330. The transferring can be effected in a partial vacuum.

This process transfers the nucleotide particles; to the target substrate 340. It is on the target substrate that the nucleotide compounds are coupled to the termini of growing polymer chains. If desired, prior to coupling, the particles can be neutralized on the target substrate after the transfer process, e.g., by passing through an alternating electric field generated by a corotron driven by AC voltage.

To insure that nucleotide particles as patterned by the photoreceptors on the interim substrate are added to the correct positions on the target substrate, the interim substrate and the target substrate are aligned prior to the transferring, e.g., with a tolerance of less than 5 or 1 μm. An appropriate tolerance can be based on the size of the array features. Means for aligning the interim substrate and the target substrate include: electrical contacts which complete a circuit when they are in apposition, a magnetic field generator and sensor, and/or mechanical male and female adaptors. In addition, alternative methods for transferring may be used, e.g., physical contact or vacuum suction (e.g., if the target substrate is porous).

Coupling

The coupling of a dry deposit of a nucleotide compound can be effected by dissolving the deposit in a solution that includes an activator compound. The activator compound can be. The activator compound can also be 5-(p-nitrophenyl)-1H-tetrazole, 5-ethylthio-1H-tetrazole, another tetrazole derivative, 4,5-dichloroimidazole, benzimidazolium triflate, or 4,5 dicyano-imidazole. For some implementations, 5-ethylthio-1H-tetrazole is particularly useful. The solvent, in which the activator is dissolved can be an organic solvent, e.g., acetonitrile, dinitriles, such as succinonitrile, glutaronitrile, adiponitrile, pimelonitrile; diethyl carbonate; and propylene carbonate.

The activator compound can be applied as an aerosol. In some cases, it is helpful to prepare the activator compound in a liquid medium that is a mixture of at least two solvents, e.g., at least two aprotic solvents, an aprotic low boiling point solvent and an aprotic high boiling point solvent, e.g., in ratios between 10:90 and 90:10 or 20:80 and 80:20. Examples of high boiling point solvents that can be used include: dinitriles, such as succinonitrile, glutaronitrile, adiponitrile, pimelonitrile; diethyl carbonate; and propylene carbonate. Examples of low boiling point solvents that can be used include: acetonitrile and methylene chloride. The high boiling point solvent may prevent evaporation of the activator compound from the aerosol whereas the low boiling point solvent facilitates aerosolization.

The activator compound can also be applied, e.g., by immersion in a solution that includes the compound across the target substrate, by pipetting a solution that includes the compound onto the target substrate, or by flowing a solution that includes the compound across the target substrate.

When dry deposits of the nucleotide compounds are dissolved in droplets of activator compounds dispensed by an atomizer, the compounds are rapidly activated and couple to the reactive groups on the target substrates. This reaction results in the formation of covalent bonds with functional groups on the surface of the target substrate. In applying a first layer of nucleotide compounds to the target substrate, the compounds are reacted with functional groups either directly on the surface or at the termini of linker compounds. For subsequent layers, the compounds are reacted with the terminal group of the growing nucleic acid polymer.

Conditions for the chemical coupling reactions and the droplet size can be adjusted so that the reaction site is highly localized.

Figure 11A:
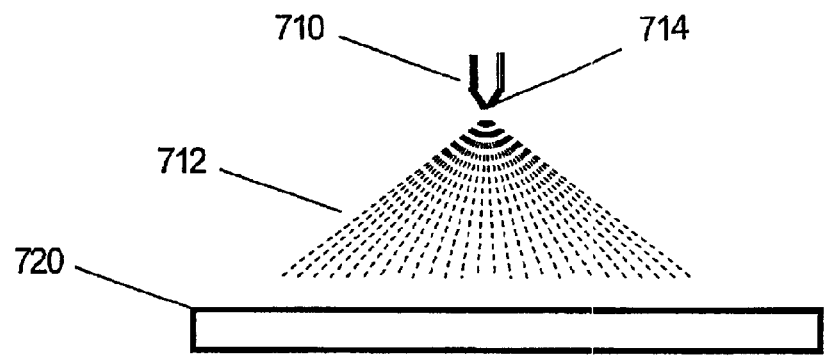
FIGS. 11A and 11B are a schematic of an exemplary device for generating an aerosol.
Figure 11B:
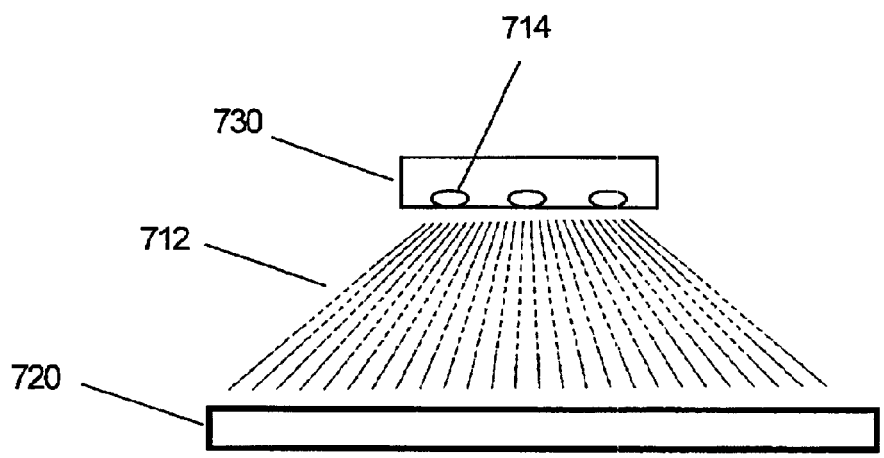

Different size sections of the target substrate or the entire target substrate can be contacted to the aerosol concurrently. Referring to the example in FIG. 11A, an aerosol generator 710 disperses an aerosol 712 through a single nozzle 714 onto the target substrate 720. Referring to the example in FIG. 11B, the aerosol generator 710 has multiple nozzles 714 that are spaced apart.

Post-processing

Following the coupling process, the target substrate is processed for one or more of the following reactions: capping, oxidation and deprotection.

Referring to FIG. 12, unreacted surface functional groups are blocked using capping reagents such as acetic anhydride in pyridine. When the surface functional group is a hydroxyl terminal, the capping reaction results in an acylated group which is blocked from further elongation of the nucleotide sequence.

Oxidation of the trivalent phosphite group can be conducted using an iodine solution (e.g., 0.05 M $I_2$ in a mixture of Py/THF/water in a ratio of 5:93:2). The trivalent phosphite bond oxidizes to form a stable pentavalent phosphate bond. Subsequently, deprotection of the nucleotide protecting group 4,4'-dimethoxytrityl (DMT) is conducted using 2% dichloroacetic acid in methylene chloride solution. Deprotection produces surface hydroxyl groups that are available for coupling with next layer of deposited nucleotide compounds.

In addition to the exemplary use of DMT, the protecting groups of the nucleic acid subunits can include photo, acid or base labile protecting groups. For example, the photolabile protecting group can be nitroveratryloxy carbonyl (NVOC), nitrobenzyloxy carbonyl (NBOC), dimethyl dimethoxybenzyloxy carbonyl, 5-bromo-7-nitroindolinyl, o-hydroxy-α-methyl cinnamoyl; 2-oxymethylene antraquinone, and methyl-6-nitropiperonyloxycarbonyl (MeNPOC) and (R,S)-(1-(3-methoxy-4-benzyloxy-6-nitrophenyl)-ethoxy) carbonyl (MBNPEOC). The photolabile protecting groups protect the nucleotide from reacting with other nucleotides or other chemical species and are photoactivatable, i.e., removable by exposure to an energy source such as UV radiation, visible radiation, electric potentials, and electron beams. The properties and uses of photolabile groups can be found, for example, in McCray et al *J. Amer. Chem. Soc.* (1970) 92:6333; Amit et al. *J. Org. Chem.* (1974) 39:192; and U.S. Pat. No. 5,889,165. U.S. Patent application Publication US2001/0044530, published Nov. 22, 2001, describes photolabile protecting groups and methods for generating 3' protecting photolabile nucleotides.

Chemical protecting groups include: 4,4'-dimethoxytrityl (DMT), fluorenylmethoxycarbonyl (Fmoc), t-butyl esters, and t-butyl ethers, e.g., t-butoxycarbonyl (t-Boc). Chemically labile protecting groups are removable by any suitable chemical method, such as acid hydrolysis. For example, Fmoc is base sensitive, whereas t-Boc and DMT are acid sensitive. Chemically labile protecting groups and chemical methods to remove these groups are described in, for example, Greene's "Protective Groups in Organic Chemistry," $2^{nd}$ Ed., published by John Wiley & Sons, New York, N.Y., 1991. Of course, the chemically labile group and the chemical conditions necessary to remove it are selected such that other linkages in the oligonucleotide, such as the connection of the first nucleotide to the linking group, are not affected when the chemically labile group is removed under specific chemical conditions.

Deprotection is tailored to the protecting group used.

Planar Supports for Chemical Synthesis

The target substrate, upon which nucleic acid subunits are coupled, is, typically, a planar solid substrate that has at least a planar surface. The surface includes reactive groups, such as carboxyl groups, amino groups, hydroxyl groups and the like. The solid surface can include a linker group such as polyethylene glycol or other carbon chains that have amide bonds or linked ether bonds. The linker groups can be of sufficient length (e.g., 5 to 60 atoms) to facilitate subunit coupling during the oligonucleotide synthesis. It usually contains 5 to 60 atoms within the linker. The linker molecule includes a terminal functional group with which surface coupling reaction occurs.

The substrate can have a rigid structure, a semi-rigid structure with flexible planar surface structure, or a non-rigid (e.g., pliable) structure. An example of a pliable glass substrate is Schott D 263 T borosilicate glass (Schott Corp., Yonkers N.Y.). The substrate can be composed of plastics, resins, silica or silica-based materials such as glass or silicon sheets. Polymeric materials such as polyvinylstyrene, polypropylene or membranous materials can also be used. Metals or metal oxides and carbons may also be used, e.g., as coatings.

In one embodiment, the substrate surface is optically transparent and has surface hydroxyl functionalities as those found on silica surface.

A planar support can also be addressable in three dimensions. For example, after synthesizing compounds in a first matrix backed by a solid support, a second matrix, providing a second plane of compounds, can be layered over the first plane. The second plane of compounds can be synthesized before or after the layering.

Array Packaging

When sheet-like substrates are used, after polymer synthesis, they can be easily diced into individual units. The units can be packaged into a cartridge or adhered to a rigid support such as glass or other materials for scanning or other detection studies.

The substrate can have any of a variety of sizes and shapes. For example, from a substrate that is 216 cm×279 cm (8.5"×11") in size, at least 20 arrays on microscopic glass slides (1"×3") can be synthesized simultaneously. In one example, the imaging technique produces at least 1.5 million unique addresses of oligonucleotides on each substrate.

As a result of the system's flexibility and demand for concurrent printing of many individual arrays, the arrays produced from a diced substrate can be all identical, or can each differ, e.g., in sequence content or level of detail.

Chemical Synthesis

The methods and apparati described here are easily adapted for generally any chemical synthesis, for which, chemical constituent compounds are available having a reactive group and a protective group. The method can be used to synthesize an array of peptides. Amino acid subunits are applied using modified amino acid which have their amino group blocked with a protecting group, e.g., t-Boc. For the second cycle, the t-Boc is removed from coupled amino acids, e.g., by deprotection of the t-Boc group with acid, e.g., trifluoroacetic acid (TFA).

A diverse collection of chemicals can be synthesized as an addressable array. These include compounds other than nucleic acids and polypeptides. See, e.g., DeWitt et al. (1993) *Nature* 90:6909; and Bunin et al. (1994) 91:4708. For example, the synthesized compounds can be formed from subunits such as 2-aminobenzophenones, natural and unnatural amino acids, and alkylating agents.

One challenge for the synthesis of chemical compounds that are not formed from linear changes of monomer subunits is the generation of diversity at different positions on a backbone compound. This challenge can be approached by depositing the backbone compound in a form modified with a variety of protecting groups, each sensitive to a different condition (e.g., light, acid, and base). First, only one of the protecting groups is removed. The dry deposition process is then used to first layer compounds for addition to a first position. Subsequently, a second protecting group is removed, and a second layer is of compounds is deposited in order to couple them to a different position on the same backbone molecule. The method can be repeated, and further, each layer of compounds can themselves be modified with protecting groups.

In addition, with respect to nucleic acid synthesis, as seen above, a variety of different coupling chemistries besides phosphoramidite chemistry can be used. The methods can also be combined with subunits other than monomers, e.g., pre-formed dimers and unnatural nucleotides.

Regarding the use of monomers as well as larger subunits, the subunit derivatives that are used can be chosen to produce nucleic acids of a particular orientation relative to the target substrate. For example, when C-3'-DMI protected, C-5'-phosphoramidite monomeric nucleotides are used to perform the oligonucleotide synthesis, the coupling is in the C-5' to C-3' direction where C-5' is attached to the solid surface and the C-3' is at the terminal position. When C-5'-DMT-C-3'-phosphoramidite monomeric nucleotides are used instead, the coupling will be in the C-3' to C-5' direction where C-3' is attached to the solid surface and the C-5' remains at the terminal position.

Software and Systems

The invention also features computer systems and software, e.g., to design, and layout biopolymer sequences for arrays, and to control an apparatus to deposit chemical subunits on a substrate.

Figure 19:
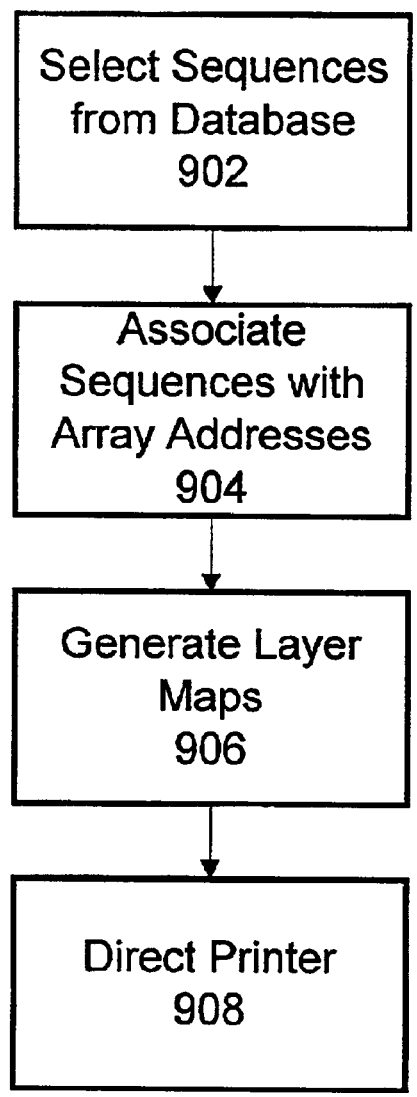

As shown in FIG. 19, a software can be used for one or more of the following procedures: selecting 902 biopolymer sequences from a sequence database; associating 904 the selected sequences with particular addresses on the target array; generating layer maps 906; and directing 908 array printing, e.g., by sending image maps derived from each layer map to applicator units.

The software can include a user interfaces that enables the user to connect to public and private databases and select individual or collections of sequences by a variety of queries, including subject matter searches and expression localization information, as well as sequence information. The user interface can also include sliders, buttons, and other graphical features, e.g., to allow the specification of parameters such as feature size, reagent concentrations, and so forth. Also, the software can prompt the user for design options, e.g., size of each address, spacing, number of addresses, sequence composition and so forth.

Once designed, the software processes the design to generate 906 layer maps 820*a*, 820*b*, 820*c*, 820*d* and to process each map (e.g., by rasters), e.g., to produce image maps that can control a light source that projects a processed layer map onto a photoreceptor to produce an image for a particular monomer addition.

Referring to the example in FIG. 18, sequence information 805 that includes four sequences (SEQ1, SEQ2, SEQ3, and SEQ4) is interpreted. Each sequence is assigned 904 to an address of a target substrate 810. In this example SEQ1 is assigned to the address 812*a*, SEQ2 to 812*b*, SEQ3 to 812*c*, and SEQ4 to 812*d*. Each register (REG) is used to generate 906 a layer map 820*a*, 820*b*, 820*c*, 820*d*. For example, with respect to the second register, the layer map 820*b* indicates C A T and G at the addresses 820*a*, 820*b*, 820*c*, 820*d* respectively. This layer map 820*b* is interpreted to create four image maps, one for each nucleotide subunit, 830*a* for the adenine subunit, 830*g* for guanine, 830*c* for cytosine, and 830*t* for thymidine. The image maps direct 908 a corresponding applicator unit to deposit the nucleotide subunit at particular positions in order to support formation of the array. In some implementations, the image map provides a set of rasterized triggers a scanning modulating laser or a light-emitting diode array, in order to direct illumination to selective regions of a photoreceptor configured for application of a particular monomer.

As the methods are adaptable for on-demand printing, they can be used to print oligonucleotide image patterns in a very flexible way. Similar to producing pages of text from a word processor to a laser printer, the printing technique described here can be used to fabricate arrays of any desired sequence of oligonucleotides by inputs to a computer, e.g., from a keyboard, mouse selection, computed or intelligent selection, or by a remote system, e.g., a second computer networked to the first computer. The computer system can include various software adaptors, e.g., to download sequences from public and private databases, and to identify useful oligonucleotide sequences from such data for inclusion on an array. Further the pattern, e.g., arrangement and size of the printed oligonucleotides can be modified according to the intended use of the oligonucleotide array.

Features of the invention can be implemented in digital electronic circuitry, or in computer hardware, firmware, software, or in combinations thereof. Methods can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD-ROM disks. Any of the foregoing can be supplemented by, or incorporated in, ASICs (application-specific integrated circuits).

Figure 17:
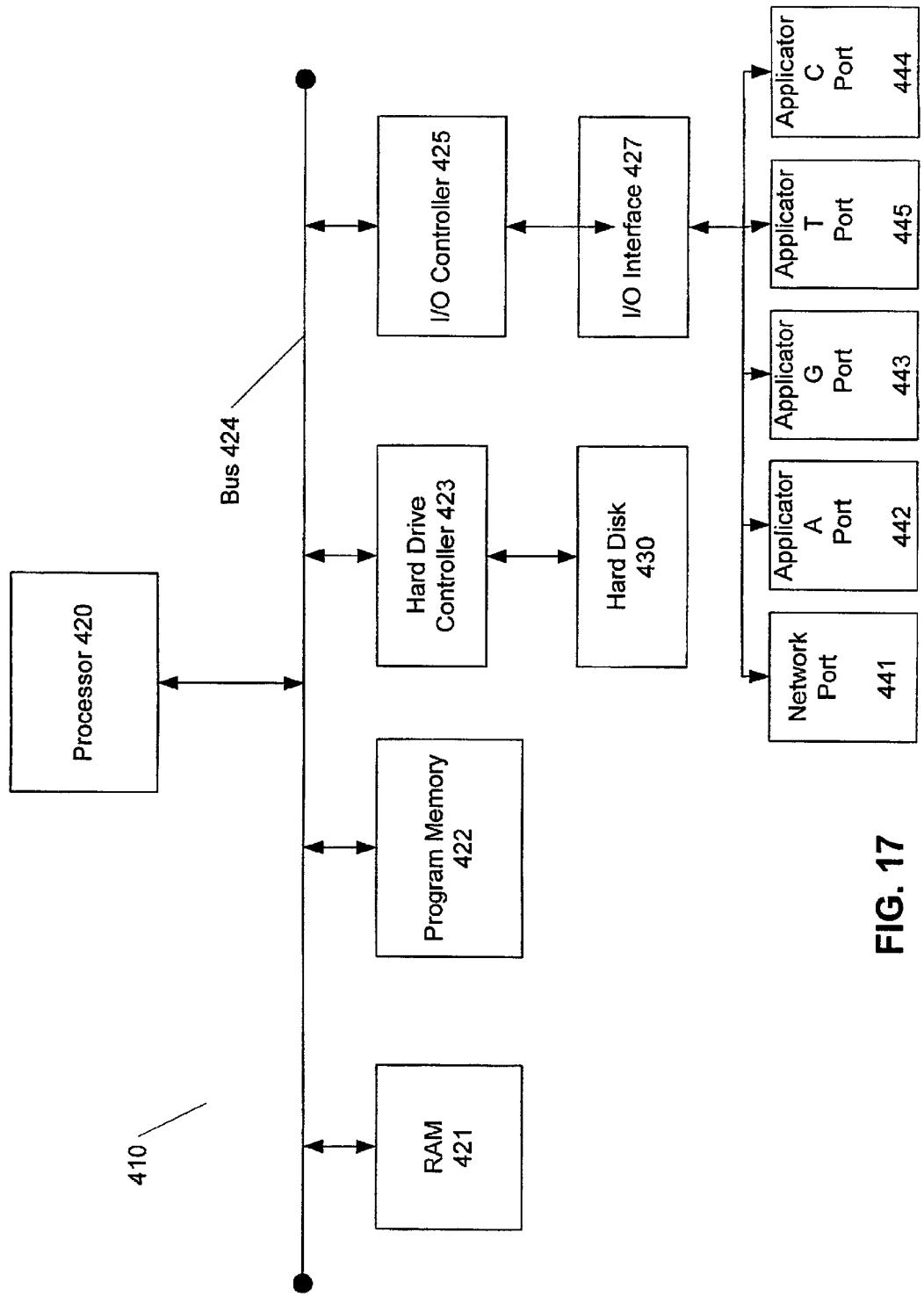
FIG. 17 is a block diagram of an exemplary controller.

An example of one such type of computer is shown in FIG. 17, which shows a block diagram of a programmable processing system (system) 410 suitable for implementing or performing the apparatus or methods of the invention. The system 410 includes a processor 420, a random access memory (RAM) 421, a program memory 422 (for example, a writable read-only memory (ROM) such as a flash ROM), a hard drive controller 423, and an input/output (I/O) controller 424 coupled by a processor (CPU) bus 425. The system 410 can be preprogrammed, in ROM, for example, or it can be programmed (and reprogrammed) by loading a program from another source (for example, from a floppy disk, a CD-ROM, or another computer).

The hard drive controller 423 is coupled to a hard disk 430 suitable for storing executable computer programs, including programs embodying the present invention, and data including storage. The I/O controller 424 is coupled by means of an I/O bus 426 to an I/O interface 427. The I/O interface 427 receives and transmits data in analog or digital form over communication links via a network port 441 such as a serial link, local area network, wireless link, and parallel link. In some implementations, the I/O interface 427 also communicates directly with at least four applicator units, e.g., via the port 442 which is in signal communication with the applicator unit for adenine addition (A); the port 443 in communication with the unit for G, port 445 in communication with the unit for T, and port 444 in communication with the unit for C.

One non-limiting example of an execution environment includes computers running Windows NT 4.0 (Microsoft) or better or Solaris 2.6 or better (Sun Microsystems) operating systems.

Exemplary Applications

Oligonucleotide arrays can be used for a variety of applications.

Recent advances in genomics have resulted in the sequencing of the genomes of many prokaryotic and of several eukaryotic organisms are available. Two drafts of the human genome sequence have been published (International Human Genome Sequencing Consortium, "Initial Sequencing and Analysis of the Human Genome", Nature 409, 860–921; 2001 and Venter J. C., et al. "The Sequence of the Human Genome"; Science 291, 1304–1350; 2001). Genome and transcriptome sequence information is a useful basis for analyzing information about the expression of genes, the function of gene products, and the relevance of genetic polymorphisms. For example, gene expression profiling (see, e.g., Lockhart D. J. and Winzler E. A; *Nature* 405, 827–836; 2000) can be used to identify cells and conditions which express particular genes. Genetic polymorphisms can be used to identify associations between the genotype of individuals and disease susceptibility or responses to drugs (see, e.g., Kruglyak L., *Nature Genetics* 22, 139–144; 1999).

Nucleic acid arrays are useful for multiplex analysis of both gene expression and genetic polymorphisms. For example, nucleic acid arrays can be fabricated by attaching or synthesizing a large number of cDNAs or synthetic oligonucleotides on a surface at precise locations (for reviews see Gerhold D. et al., *TIBS* 24, 168–173; 1999 and Watson A. et al., *Current Opinion in Biotechnology* 9, 609–614; 1998). Upon the binding of nucleic acid samples to specific features of the array, signals are generated and detected (Basarsky T. et al.; in "Microarray Biochip Technology, M. Schena, Ed., Eaton Publishing, Natick, Mass.; 2000).

One type of oligonucleotide array is a primer array in which the oligonucleotides are attached by their 5' terminus to the array solid support. The oligonucleotides on such arrays can be used as primers in primer extension reactions. Assays based on primer extension can be used for genotyping single nucleotide polymorphisms (SNPs). (See Thomas A. Weaver, *"High-throughput SNP Discovery and Typing for Genome-wide Genetic Analysis"*, Trends in Genetics, December 2000).

Arrays of polypeptide compounds are useful for screening ligands for a target compound. The identified ligands may be a lead for drug discovery. Arrays of non-polymeric compounds are similarly useful for drug discovery screens. Other arrays can be used as sensors, e.g., an environmental sensor or as a diagnostic tool, e.g., to detect the presence of particular antigens.

The following specific examples are merely illustrative, and not limitative of the scope of the invention. All publications, references, patents, and patent applications cited herein are incorporated in their entirety by reference.

EXAMPLE 1

A solution of 0.25 M of 3'-DMT-thymidine-5'-CEP in acetonitrile was prepared with 0.37 grams of 3'-dimethoxytrityl-5'-phosphoramidite-deoxythymidine dissolved in 2 ml of distilled, anhydrous acetonitrile in a dry box. A microscopic glass slide was covalently coated with polyethylene glycol. The glass slide was dried and stored in dry box. The 3'-O-DMT-thymidine-5'-phosphoramidite solution was spotted onto the glass slide in an arrayed format at four different concentrations (25, 50, 100 and 250 mM) and at different volumes (0.1, 0.25, 0.5 and 1 ul). The slide was dried in the dry box until a thin-film of 3'-O-DMT-thymidine-5'-phosphoramidite developed on the glass surface. The glass slide was then dipped into a solution of 0.5 M tetrazole in dry acetonitrile. The slide was washed with acetonitrile, oxidized with 50 mM iodine solution (THF/Py/Water in 93/5/2 ratio) for 3 minutes. The slide was thoroughly washed again with acetonitrile, dried and replaced in the dry box. The slide was spotted with a solution of 40 mM Cy3 Amidite (Amersham Pharmacia), a fluorescence labelling reagent, in acetonitrile and 200 mM tetrazole in acetonitrile. Labelling with Cy3 amidite indicates immobilized reactive groups on the substrate which failed to react with the thymidine deposited as a thin film.

The resulting slide was then washed with acetonitrile, methanol and SSPE buffer. The slide was inserted into a laser scanner, ScanArray (GSI Lumonics) excited at 540 nm. The percentage relative light units (% RLU) were determined. The results demonstrated that 3'-O-DMT-thymidine-5'-phosphoramidite was indeed coupled to the glass slide and the higher the compound concentration the better the coupling yield. At concentration closer to 100 mM, the coupling almost reached saturation. See also FIG. 14 and Example 1 of U.S. Provisional Patent Application Ser. No. 60/279,004, filed Mar. 26, 2001.

EXAMPLE 2

As described for the thin-film of 3'-O-DMT-thymidine-5'-phosphoramidite compound developed on the glass surface in Example 1, the following experiment indicated that immersion of the glass slide in 0.5 M of tetrazole solution in acetonitrile did not cause a dissolution and diffusion of the thin-film compound into the tetrazole solution.

A 0.25 M solution containing 3'-O-DMT-thymidine-5'-phosphoramidite in acetonitrile was used to spot on a glass slide which was previously coated with polyethylene glycol. A fluorescence labeling Cy3 solution was applied and the glass slide was scanned through a laser scanner, ScanArray (made by GSI Lumonics). A blue circle and a yellow circular background was observed. The blue circle indicated that the spot was covered by the DMT protected thymidine compound which was covalently attached to the blue spot. The yellow background indicated the presence of the unreacted linker molecules containing the free hydroxyl group which reacted with the Cy3 Amidite. The clear and discrete boundary between the blue circle and the yellow background indicated that there is no diffusion of the physically coated 3'-O-DMT-thymidine-5'-phosphoramidite compound when the reagent spotted glass slide was immersed in the tetrazole solution. This experiment demonstrated that while the spot coated thymidine phosphoramidite compound dissolved in tetrazole solution, it was activated instantaneously and reacted with the hydroxyl groups on the glass surface. See also FIG. 15 and Example 1 of U.S. Provisional Patent Application Ser. No. 60/279,004, filed Mar. 26, 2001.

EXAMPLE 3

The 5'-DMT-dA-($\beta$-cyanoethyl)-phosphoramidite compound was pulverized using a jet mill and sorted using a classifier to collect powders with different, predefined particle size. The charge characteristics of a processed nucleotide sample, LT-511-811-1 (5'-DMT-dA-($\beta$-cyanoethyl)-phosphoramidite), was measured using a charge spectrometer q-test, made by Epping, GmbH, Germany. This positively charged sample had a q/d value of 28 fC/$\mu$m.

Similar samples, L30 and L38 were used as a toner in a print engine on Kyocera model 8000 which is designed for use with positive toners. Although usable, the triboelectric charge of these samples decreased after only a few prints.

To improve the charge characteristics, surface charge control agents and one of the selected triboelectric series such as polystyrene were used as additives. The procedure is described as follows.

1. Hercules D125 polystyrene was jet milled to 7.8 micron average diameter. It was then classified to obtain a preparation of approximately 70% >5 micron (percentage by number). The jet mill used was the Page: 41 [0]Trost™ TX jet mill (from Plastomer Products, Newtown)

2. The nucleotide powder was jet milled and classified to collect the finest particle fraction (typically less than 3 microns diameter) in a filter bag. Classifiers that can be used include: Alpine® 100 MZR Classifier (from Hosokawa Micron Power System, Summit, N.J.).

3. Fine nucleotide particle/Silica blends were produced by blending 4 grams of fine nucleotide powders and 1 g of Degussa R504 fumed silica at medium speed in a Sorvall blender.

4. 1 gram of blended nucleotide powders/fumed silica from (step 3) was blended for 2×5 sec with 40 g of polystyrene powder from step 1.

5. 0.35% Pennwalt Kynar 461 is added to this blend and mixed 2×5 sec. to produce the final nucleotide toner preparation.

6. A "treated" carrier is prepared by mixing 3000 g Powdertech carrier DMO70C silicone coated ferrite with 0.65 g R504 fumed silica and 0.2 g 812 fumed silica for 1 hour (e.g., about 0.5% R504 fumed silica; and 0.1% 812 fumed silica).

7. A developer is prepared by blending 30 grams of the final nucleotide toner from step 4 with 570 grams of treated carrier for 1 hour.

The exemplary final toner preparation (e.g., from step 5) includes about 2% nucleotide particles; 0.5% fumed silica; 97% polystyrene powder; 0.35% Knyar. The toner preparation is then combined with the treated carrier to form the developer, e.g., as described in steps 6 and 7.

The resulting mixtures were then subjected to the measurement of electrostatic charge distribution using the q-test apparatus and the Trek Q/M device (Model 210HS). This nucleotide developer preparation maintained a stable positive charge after triboelectric charging.

The two samples L47-A (adenyl compound) and L47-T (thymidyl compound) nucleotide developer compositions also gave stable charge characteristics and maintained acceptable charge even after 1200 prints. The particular qualities of these toner can be further controlled by variation of the particular agents selected (e.g., the surface charge control agent) and the ratios.

EXAMPLE 4

Printing Nucleotide Particles

Figure 15:
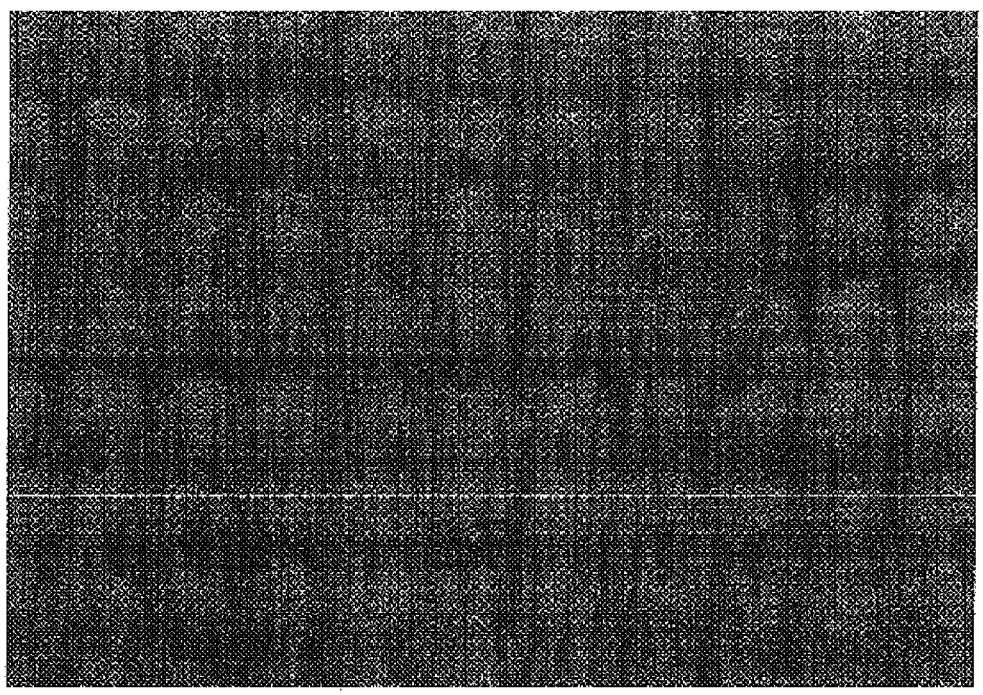
FIGS. 15 and 16 are images of printed substrates.

An electrophotographic print machine purchased from Kyocera model 8000 was modified to accommodate the positively charged nucleotide toners, the user interface for printing specific array format. In addition, the physical fusion mechanism was eliminated. The four nucleotide toners, each contained one of the four nucleotide monomers dA, dT, dG and dC, were placed in toner compartments. Those four nucleotide toners were prepared according to the procedures described in Example 3. The latent image created on the photoreceptor was introduced from a software program designed to provide image layers converted from a set of selected oligonucleotide sequences. A set of arrays containing 400,000 image spots was used as an example in the printing process. The printing was conducted using an interim substrate such as the transparency sheet (e.g., Model PP 2200 and PP 2500 from 3M®). After the printing, the nucleotide toners image was transferred to a glass substrate through a scanning corotron which was induced with 6,000 DC voltage. As shown in FIG. 15, the resulting nucleotide image on the glass substrate contained the corresponding 400,000 spots and the location of each spot contained nucleotide powder addressed at predefined position according to the image design layout from the software program. In this case, each spot is 150 $\mu$m in diameter with a pitch of 300 $\mu$m. The software program also allows one to produce spot sizes from 50 $\mu$m to 500 $\mu$m in diameter anywhere on the same substrate. The spots can be any shape, e.g., circular, elliptical, rectangular, or square. The flexibility to choose spot size and sequence offers advantages for the optimization of the subsequent hybridization experiment.

EXAMPLE 5

Chemical Fusion

After the image transfer to the glass substrate was conducted as described in Example 4, arrays of the nucleotide phosphoramidites were ready to be chemically "fused" to the substrate surface. The glass substrate was subjected to a moisture controlled chamber where an apparatus containing an atomizer was installed. The atomizer was attached to a pressurized reagent bottle. Other means for making a mist include: a sonicator and a piezoelectric dispenser. The reagent was prepared from a solution containing 0.4 M of tetrazole in a mixed solvent that includes acetonitrile and propylene carbonate in a 60/40 ratio.

When the pressure was applied, the atomizer produced a very fine mist of the chemical reagent. The fine mist contacted the substrate surface created the reagent droplets of approx. 10 $\mu$m in diameter. As soon as arrays of the nucleotide powders were in contact with the reagent droplets, the nucleotide powders instantaneously dissolved and activated by the reagent droplets. The activated nucleotide then immediately reacted with the surface of the glass substrate. The whole processes occurred within about 10 seconds after the atomizer was applied to the glass substrate. Coupling of the activated nucleotides with the surface hydroxyl groups on the glass substrate formed the basis of chemical fusion of the nucleotides with the substrate. After the fusion reaction, the glass substrate was immersed in a bath of methanol to quench the unreacted reagent on the substrate surface. The substrate was washed thoroughly with methanol and dried for the next surface chemical operations.

In order to ensure high coupling yield of the nucleotides in each layer, the procedure used in Example 4 and 5 can be repeated with the same image layer on the substrate. Multiple couplings can be used to improve the quantitative yield, although it may not be necessary

EXAMPLE 6

Capping

Figure 12:
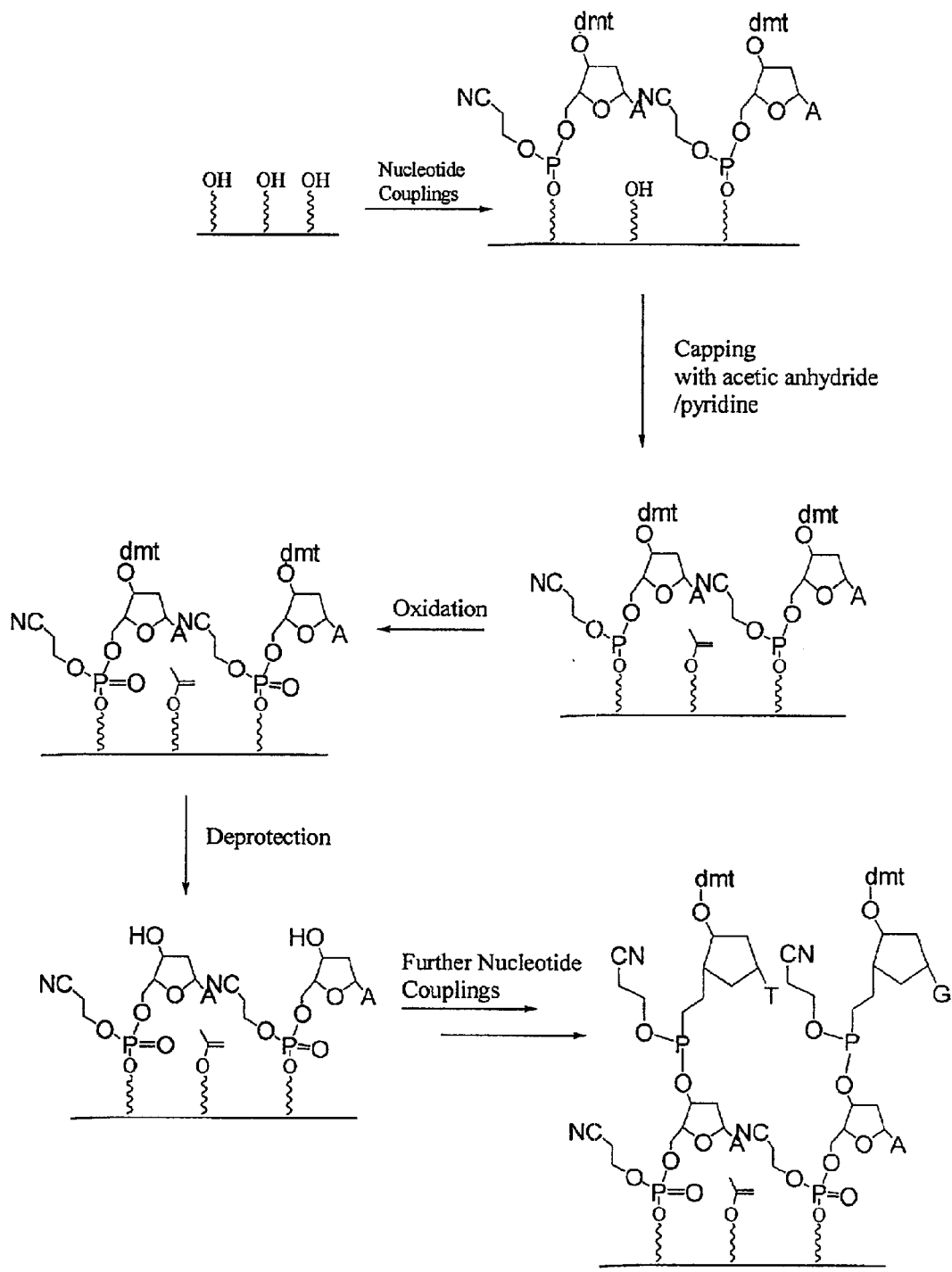
FIG. 12 depicts an exemplary process for capping of unused reactive groups.

After the chemical fusion of the printed arrays was accomplished as described in Example 5, the glass substrate was immersed in a reagent bath containing a mixture of 1:1 ratio of acetic anhydride and pyridine for 5 minutes. As shown in FIG. 12, the surface hydroxyl groups outside the toner image area were inactivated by acylation. This created a predefined size and location of the nucleotide arrays. The array substrate was then washed two times with methanol and air dried.

EXAMPLE 7

Oxidation and Deprotection

The array substrate obtained from Example 6 was immersed in a bath containing oxidation reagent prepared from an iodine solution (0.05 M $I_2$ in a mixture of Py/THF/water in a ratio of 5:93:2) for 2 minutes. The substrate was then washed thoroughly with methanol and air dried. Deprotection of the nucleotide protecting groups 4,4'-dimethoxytrityl (DMT) was conducted by immersing again the glass substrate in a bath containing 2% dichloroacetic acid in methylene chloride solution for 1 minute. The array substrate was washed twice with methylene chloride and dried for 2 minutes in an oven maintained at 50° C. In order to examine that the arrayed nucleotides were covalently coupled to the glass substrate, the glass substrate was immersed in an activated Cy3 reagent for 20 seconds. The activated Cy3 reagent was prepared from mixing an acetonitrile solution containing 100 mg of Cy3 phosphoramidite and another solution containing 0.4 M of tetrazole in acetonitrile. The Cy3 treated glass substrate was washed with acetonitrile and subjected to a laser scanning instrument, ScanArray, made by Packard BioSciences. The scanned image clearly indicated the presence of nucleotides covalently attached to the substrate surface with the same array image.

EXAMPLE 8

Synthesis of an Oligonucleotide Array

A glass slide (25×75 mm), pre-coated with polyethylene glycol (MW ca. 400), was spotted with a solution of 5'-dimethoxytrityl-3'-[(2-cyanoethyl)-(N,N-diisopropyl)]-phosphoramidite of 2'-deoxynucleoside (0.1M in acetonitrile). The spotting was performed on a Cartesian MicroSys™ SQ 4000 System (Cartesian Technologies, Inc.) according to the manufacturer's operating manual. This device uses a solenoid to deposit solutions of phosphoramidite nucleotides. After spotting, the slide was heated at 80° C. for 5 minutes to evaporate the solution and form a dry film of the phosphoramidite nucleotide. The slide was subsequently transferred to a glove box purged with nitrogen gas.

The phosphoramidite derivative of the nucleoside was coupled to the polyethylene glycol linker on the glass slide as follows. The glass slide was sprayed with an aerosol of 0.4M tetrazole solution in an organic solvent through a spray head for 10 seconds. The reaction was continued for 2 minutes at ambient temperature and the glass slide was thoroughly washed in acetonitrile. The unreacted functional groups on the slide were capped with a solution of 1.1M 1-methylimidazole, 0.66M acetic anhydride, and 0.54M 2,6-lutidine in tetrahydrofuran for 2 minutes. The slide was then removed from glove box and washed twice with acetonitrile. The phosphite triester was oxidized with 50 mM iodine in a mixture of tetrahydrofuran-pyridine-water (93:5:2) for 1 minute. After washing with acetonitrile twice, the dimethoxytrityl protecting groups of the nucleotides were removed by treating the slide with 2% dichloroacetic acid in methylene chloride for 1 minute. The slide was then washed with acetonitrile twice and dried at 80° C. for 5 minutes. The slide was subsequently placed on the (Cartesian system for another cycle of spotting. These processes is repeated to synthesize the numerous different DNA sequences on the array.

A 4×6 array with 1.5 mm spacings was constructed using 20 µl spots and the method described above. The protecting groups were removed by treating the slide with a mixture of ethylene diamine:ethanol (1:1) for 2 hours at ambient temperature. The slide was then washed with ethanol, de-ionized water, acetone, and dried in air. Two different octamer nucleic acid sequences that differ by only a single nucleotide were synthesized on the array. The array was then tested by hybridization with a Cy3 dye labeled probe that was exactly complementary to one of the two octomer sequences. The probe sequence, nucleic acid sequences on the array, and hybridization results are detailed in U.S. application Ser. No. 60/322,362, filed Sep. 14, 2001.

The probe was hybridized to the array at 25° C. for 3 hours in a humidity chamber. The slide was washed with 5×SSPE buffer for 1 minute, air dried, and scanned for Cy3 signals on a GSI Scan Array 4000 system (Packard Instruments). Addresses which have nucleic acids complementary to the probe, gave bright fluorescent signals indicating a significant hybridization between the synthesized oligonucleotides and the probe. Addresses that have the mismatched sequence, on the other hand, showed little signal, indicating no significant hybridization. These results confirm the fidelity of the synthetic process.

Similar results were obtained with a 12-mer sequence.

EXAMPLE 9

Protected nucleotide monomers, A, T, G, and C are spotted on surface treated microscopic glass slides. Four piezo-electric ink jet nozzle heads are used to deliver the four basic nucleotide monomers to different addresses on the slide. The microdrops of the nucleotides are dried in the air at room temperature or in an oven heated, for example, at a temperature of less than 80° C. to form thin-films, typically shaped as circular spots. The size of the spotted thin-films ranges from 20 nm to 1500 nm depending on the spotting volume.

The nucleotide monomers are protected with trityl groups at the distal end and phosphoramidites on the proximal end of the nucleotide monomers. An aerosol of 5-ethylthio-1H-tetrazole is contacted to the slide so that monomers are coupled to functional groups on the surface at the different addresses. The aerosol cloud can contact the entire slide at once.

Other Embodiments

A number of embodiments of the invention have been described. Nevertheless, it will be understood that various modifications may be made without departing from the spirit and scope of the invention. For example, other embodiments of apparati described herein can include apparati with various drums and belts inserted for transferring chemical compounds from the photoreceptor to the substrate. Further, as would be apparent to the artisan of ordinary skill, the methods described here can be adapted to the synthesis of non-polymeric compounds, e.g., addressable combinatorial chemical libraries based on a molecular scaffold. Other embodiments are within the scope of the following claims.

What is claimed:

1. A method of providing a developer composition, the method comprising:
    providing particles of a nucleotide monomer that is protected at one terminus, the particles being less than 50 µm in average diameter; and
    combining the particles with a carrier agent to provide a developer composition.

2. The method of claim 1 wherein the nucleotide monomer is activated at the other terminus.

3. The method of claim 1 wherein the providing comprises jet milling the particles.

4. The method of claim 1 wherein the providing comprises isolating particles that are less than 10 µm in diameter.

5. The method of claim 1 wherein the carrier agent comprises ferrite carrier beads.

6. The method of claim 1 further comprising, combining the particles with a surface charge control agent.

7. The method of claim 6 wherein the surface charge control agent includes one or more of: cabosil, fumed silica, a fluorinated polymer, and polystyrene.

8. The method of claim 1 wherein the particles are less than 10 µm in average diameter.

9. A method for transferring nucleotide particles from a surface to a substrate comprising:

providing a composition that comprises: (a) chargeable particles of less than 50 microns diameter, the particles include a nucleotide compound that has a phosphoramidite group and a protecting group, and (b) chargeable carrier beads;

triboelectrically charging the nucleotide particles;

contacting the charged nucleotide particles to a selectively charged surface; and transferring the nucleotide particles from the surface to a substrate.

10. The method of claim 9 wherein the selectively charged surface comprises discrete areas that electrostatically repel the charged nucleotide particles and other areas to which the charged nucleotide particles attach.

11. The method of claim 9 wherein the selectively charged surface is cylindrical.

12. The method of claim 9 wherein the selectively charged surface is the surface of a belt.

13. The method of claim 9 wherein the selectively charged surface is a photoreceptor.

14. The method of claim 8 wherein the charging charges the nucleotide particles to between 5 $\mu C/g$ to 50 $\mu C/g$.

15. The method of claim 8 wherein the composition further comprises (c) a surface charge control agent.

* * * * *